US012702719B2

(12) United States Patent
Mirkin et al.

(10) Patent No.: US 12,702,719 B2
(45) Date of Patent: Aug. 11, 2026

(54) HAIRPIN-LIKE OLIGONUCLEOTIDE-CONJUGATED SPHERICAL NUCLEIC ACID

(71) Applicant: NORTHWESTERN UNIVERSITY, Evanston, IL (US)

(72) Inventors: Chad A. Mirkin, Wilmette, IL (US); Gokay Yamankurt, Chicago, IL (US); Matthew K. Vasher, Pickney, MI (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 692 days.

(21) Appl. No.: 17/435,903

(22) PCT Filed: Mar. 5, 2020

(86) PCT No.: PCT/US2020/021275
§ 371 (c)(1),
(2) Date: Sep. 2, 2021

(87) PCT Pub. No.: WO2020/181144
PCT Pub. Date: Sep. 10, 2020

(65) Prior Publication Data
US 2022/0175956 A1 Jun. 9, 2022

Related U.S. Application Data

(60) Provisional application No. 62/814,569, filed on Mar. 6, 2019.

(51) Int. Cl.
*A61K 47/69* (2017.01)
*C12N 15/113* (2010.01)

(52) U.S. Cl.
CPC ...... *A61K 47/6923* (2017.08); *A61K 47/6937* (2017.08); *C12N 15/1138* (2013.01); *C12N 2310/122* (2013.01); *C12N 2310/14* (2013.01); *C12N 2310/351* (2013.01)

(58) Field of Classification Search
CPC ............ A61K 47/6923; A61K 47/6937; C12N 15/1138; C12N 2310/122; C12N 2310/14; C12N 2310/351; C12N 2310/318; C12N 2310/51; C12N 2320/32; C12N 15/111
See application file for complete search history.

(56) References Cited

U.S. PATENT DOCUMENTS 3,687,808 A 8/1972 Merigan et al.
4,469,863 A 9/1984 Ts et al.
4,476,301 A 10/1984 Imbach et al.
4,489,055 A 12/1984 Couvreur et al.
4,845,205 A 7/1989 Huynh et al.
4,981,957 A 1/1991 Lebleu et al.
5,008,050 A 4/1991 Cullis et al.
5,023,243 A 6/1991 Tullis
5,034,506 A 7/1991 Summerton et al.
5,118,800 A 6/1992 Smith et al.
5,130,302 A 7/1992 Spielvogel et al.
5,134,066 A 7/1992 Rogers et al.
5,166,315 A 11/1992 Summerton et al.
5,175,273 A 12/1992 Bischofberger et al.
5,177,196 A 1/1993 Meyer et al.
5,185,444 A 2/1993 Summerton et al.
5,188,897 A 2/1993 Suhadolnik et al.
5,194,599 A 3/1993 Froehler et al.
5,214,134 A 5/1993 Weis et al.
5,216,141 A 6/1993 Benner
5,235,033 A 8/1993 Summerton et al.
5,264,423 A 11/1993 Cohen et al.
5,264,562 A 11/1993 Matteucci
5,264,564 A 11/1993 Matteucci
5,264,618 A 11/1993 Felgner et al.
5,276,019 A 1/1994 Cohen et al.
5,278,302 A 1/1994 Caruthers et al.
5,286,717 A 2/1994 Cohen et al.
5,319,080 A 6/1994 Leumann
5,321,131 A 6/1994 Agrawal et al.
5,359,044 A 10/1994 Cook et al.
5,367,066 A 11/1994 Urdea et al.
5,393,878 A 2/1995 Leumann
5,399,676 A 3/1995 Froehler
5,405,938 A 4/1995 Summerton et al.
5,405,939 A 4/1995 Suhadolnik et al.
5,432,272 A 7/1995 Benner
5,434,257 A 7/1995 Matteucci et al.
5,446,137 A 8/1995 Maag et al.
(Continued)

FOREIGN PATENT DOCUMENTS

AU 64763/98 A 7/1998
CA 2787156 A1 7/2011
(Continued)

OTHER PUBLICATIONS

Patel et al., Scavenger receptors mediate cellular uptake of polyvalent oligonucleotide-functionalized gold nanoparticles, Bioconjugate Chem., 21(12):2250-2256 (2010).
Patnaik et al., Phase 1 study of pembrolizumab (pembro; MK-3475) plus ipilimumab (IPI) as second-line therapy for advanced non-small cell lung cancer (NSCLC): KEYNOTE-021 cohort D, Journal of Clinical Oncology 33 (15):8011-8011 (2015).
Patrie et al., Self-assembled monolayers for MALDI-TOF mass spectrometry for immunoassays of human protein antigens, Anal. Chem., 79:5878-87 (2007).
Patterson et al., Use of the green fluorescent protein and its mutants in quantitative fluorescence microscopy, Biophys. J., 73(5):2782-2790 (1997).
(Continued)

*Primary Examiner* — Robert A Wax
*Assistant Examiner* — Ngoc-Anh Thi Nguyen
(74) *Attorney, Agent, or Firm* — MARSHALL, GERSTEIN & BORUN LLP

(57) ABSTRACT

The disclosure is generally related to oligonucleotides having a hairpin-like structure, nanoparticles comprising the same, and methods of using the same.

20 Claims, 18 Drawing Sheets

Specification includes a Sequence Listing.

(56) References Cited

U.S. PATENT DOCUMENTS 5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,502,177 A 3/1996 Matteucci et al.
5,514,785 A 5/1996 Van et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,539,082 A 7/1996 Nielsen et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,555 A 10/1996 Froehler et al.
5,567,811 A 10/1996 Misiura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,591,722 A 1/1997 Montgomery et al.
5,594,121 A 1/1997 Froehler et al.
5,596,086 A 1/1997 Matteucci et al.
5,596,091 A 1/1997 Switzer
5,597,909 A 1/1997 Urdea et al.
5,602,240 A 2/1997 Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,645,985 A 7/1997 Froehler et al.
5,646,265 A 7/1997 McGee
5,646,269 A 7/1997 Matteucci et al.
5,658,873 A 8/1997 Bertsch-Frank et al.
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,700,920 A 12/1997 Altmann et al.
5,714,331 A 2/1998 Buchardt et al.
5,719,262 A 2/1998 Buchardt et al.
5,721,218 A 2/1998 Froehler
5,750,692 A 5/1998 Cook et al.
5,763,588 A 6/1998 Matteucci et al.
5,792,608 A 8/1998 Swaminathan et al.
5,792,747 A 8/1998 Schally et al.
5,814,666 A 9/1998 Green et al.
5,830,653 A 11/1998 Froehler et al.
5,955,589 A 9/1999 Cook et al.
6,005,096 A 12/1999 Matteucci et al.
6,051,698 A 4/2000 Janjic et al.
6,239,116 B1 5/2001 Krieg et al.
6,271,209 B1 8/2001 Smith et al.
6,406,705 B1 6/2002 Davis et al.
6,677,153 B2 1/2004 Iversen
7,223,833 B1 5/2007 Nielsen et al.
7,238,472 B2 7/2007 Mirkin et al.
7,605,251 B2 10/2009 Tan et al.
7,615,539 B2 11/2009 Uhlmann et al.
7,667,004 B2 2/2010 Zhong et al.
7,833,992 B2 11/2010 Vargeese et al.
8,252,756 B2 8/2012 Rosi et al.
8,440,811 B2 5/2013 Chang et al.
8,461,117 B2 6/2013 Sufi et al.
8,507,200 B2 8/2013 Mirkin et al.
8,664,407 B2 3/2014 Chen et al.
8,846,080 B2 9/2014 Biemans et al.
8,933,046 B2 1/2015 Machuy et al.
8,940,310 B2 1/2015 Barrat et al.
8,999,947 B2 4/2015 Mirkin et al.
9,139,827 B2 9/2015 Mirkin et al.
9,297,013 B2 3/2016 Guo
9,376,690 B2 6/2016 Mirkin et al.
9,506,056 B2 11/2016 Mirkin et al.
9,693,957 B2 7/2017 Lin et al.
9,719,089 B2 8/2017 Mirkin et al.
9,757,475 B2 9/2017 Mirkin et al.
9,816,091 B2 11/2017 Ge et al.
9,834,439 B2 12/2017 Yin et al.
9,844,562 B2 12/2017 Mirkin et al.
9,868,955 B2 1/2018 Guiducci et al.
9,889,209 B2 2/2018 Mirkin et al.
9,890,427 B2 2/2018 Mirkin et al.
9,901,616 B2 2/2018 Dhar et al.
10,098,958 B2 10/2018 Mirkin et al.
10,182,988 B2 1/2019 Mirkin et al.
10,208,310 B2 2/2019 Mader et al.
10,301,622 B2 5/2019 Mirkin et al.
10,370,656 B2 8/2019 Mirkin et al.
10,370,661 B2 8/2019 Mirkin et al.
10,391,116 B2 8/2019 Mirkin et al.
10,398,784 B2 9/2019 Mirkin et al.
10,563,244 B2 2/2020 Mrksich et al.
10,782,287 B2 9/2020 Mrksich et al.
10,792,251 B2 10/2020 Mirkin et al.
10,837,018 B2 11/2020 Radovic-Moreno et al.
10,894,963 B2 1/2021 Radovic-Moreno et al.
11,047,861 B2 6/2021 Mrksich et al.
11,123,294 B2 9/2021 Radovic-Moreno et al.
11,433,131 B2 9/2022 Mirkin et al.
11,690,920 B2 7/2023 Mirkin et al.
2002/0172711 A1 11/2002 Martin et al.
2003/0026782 A1 2/2003 Krieg
2003/0044354 A1 3/2003 Carpenter et al.
2003/0147966 A1 8/2003 Franzen et al.
2003/0170162 A1 9/2003 Nayfeh et al.
2004/0014956 A1 1/2004 Woolf et al.
2004/0033197 A1 2/2004 Madar et al.
2004/0053384 A1 3/2004 Sligar et al.
2004/0058886 A1 3/2004 Scaringe
2004/0158051 A1 8/2004 Ozkan et al.
2004/0170560 A1 9/2004 Fossheim et al.
2004/0219565 A1 11/2004 Kauppinen et al.
2005/0130167 A1 6/2005 Bao et al.
2005/0232866 A1 10/2005 Melchior et al.
2006/0014191 A1 1/2006 Lao et al.
2006/0083781 A1 4/2006 Shastri et al.
2006/0228733 A1 10/2006 Pierce et al.
2006/0292174 A1 12/2006 De et al.
2007/0218547 A1 9/2007 Yeates et al.
2007/0243136 A1 10/2007 Fisher et al.
2007/0298257 A1 12/2007 Ludwig et al.
2008/0175893 A1 7/2008 Huang et al.
2008/0181928 A1 7/2008 Hakimi-Mehr et al.
2008/0194463 A1 8/2008 Weller et al.
2008/0311182 A1 12/2008 Ferrari et al.
2009/0018028 A1 1/2009 Lindsay et al.
2009/0053169 A1 2/2009 Castillo et al.
2009/0065822 A1 3/2009 Hwang
2009/0209629 A1 8/2009 Mirkin et al.
2009/0246142 A1 10/2009 Bhatia et al.
2009/0322327 A1 12/2009 Gao
2010/0003317 A1 1/2010 Akinc et al.
2010/0092486 A1 4/2010 Kandimalla et al.
2010/0099858 A1 4/2010 Mirkin et al.
2010/0136682 A1 6/2010 Mirkin et al.

(56) References Cited

U.S. PATENT DOCUMENTS

2010/0144848 A1 6/2010 Vogel et al.
2010/0166842 A1 7/2010 Lu et al.
2010/0203149 A1 8/2010 Radosz et al.
2010/0233270 A1 9/2010 Mirkin et al.
2011/0020242 A1 1/2011 Zheng et al.
2011/0052680 A1 3/2011 Hendrickson et al.
2011/0052697 A1 3/2011 Farokhzad et al.
2011/0159081 A1 6/2011 Biemans et al.
2011/0223257 A1 9/2011 Zhao et al.
2011/0229529 A1 9/2011 Irvine et al.
2011/0237435 A1 9/2011 Ryan
2012/0149843 A1 6/2012 Chien et al.
2012/0282186 A1 11/2012 Mirkin et al.
2012/0283316 A1 11/2012 Mirkin et al.
2013/0028857 A1 1/2013 Gao et al.
2013/0089614 A1 4/2013 Zhang et al.
2013/0123333 A1 5/2013 Mirkin et al.
2013/0149374 A1 6/2013 Lee et al.
2013/0172404 A1 7/2013 Mirkin et al.
2013/0196951 A1 8/2013 Schoenfisch et al.
2013/0252852 A1 9/2013 Pfeiffer et al.
2013/0274441 A1 10/2013 King et al.
2013/0295129 A1 11/2013 Irvine et al.
2013/0309172 A1 11/2013 Suresh et al.
2013/0315831 A1 11/2013 Shi et al.
2014/0065425 A1 3/2014 Bogdanov
2014/0068429 A1 3/2014 Belbin et al.
2015/0031745 A1 1/2015 Mirkin et al.
2015/0111790 A1 4/2015 Ategeka et al.
2015/0259680 A1 9/2015 Mirkin et al.
2015/0352138 A1 12/2015 Mirkin et al.
2016/0108123 A1 4/2016 Freeman et al.
2016/0186178 A1 6/2016 Radovic-Moreno et al.
2016/0194642 A1 7/2016 Gryaznov et al.
2016/0206747 A1 7/2016 Mirkin et al.
2016/0208245 A1 7/2016 Ahn et al.
2016/0237429 A1 8/2016 Cubillos-Ruiz et al.
2016/0274134 A1 9/2016 Mutharasan et al.
2016/0281086 A1 9/2016 Mirkin et al.
2016/0310425 A1 10/2016 Mirkin et al.
2017/0137809 A1 5/2017 Mirkin et al.
2017/0157048 A1 6/2017 Radovic-Moreno et al.
2017/0232109 A1 8/2017 Mirkin et al.
2018/0072810 A1 3/2018 Afar et al.
2018/0080058 A1 3/2018 Mrksich et al.
2018/0085390 A1 3/2018 Mirkin et al.
2018/0187189 A1 7/2018 Mirkin et al.
2018/0193484 A1 7/2018 Mirkin et al.
2018/0222982 A1 8/2018 Dranoff et al.
2018/0231564 A1 8/2018 Mrksich et al.
2019/0060324 A1 2/2019 Sleiman et al.
2019/0161556 A1 5/2019 Mrksich et al.
2020/0022913 A1 1/2020 Mirkin et al.
2020/0101156 A1 4/2020 Mirkin et al.
2020/0246484 A1 8/2020 Mirkin et al.
2020/0384104 A1 12/2020 Mirkin et al.
2021/0039062 A1 2/2021 Mirkin et al.
2021/0052497 A1 2/2021 Mirkin et al.
2021/0087221 A1 3/2021 Mirkin et al.
2021/0102211 A1 4/2021 Radovic-Moreno et al.
2021/0122778 A1 4/2021 Mirkin et al.
2021/0123057 A1 4/2021 Mirkin et al.
2021/0189397 A1 6/2021 Mirkin et al.
2021/0220454 A1 7/2021 Mirkin et al.
2021/0231677 A1 7/2021 Mrksich et al.
2021/0236651 A1 8/2021 Mirkin et al.
2021/0332495 A1 10/2021 Mirkin et al.
2022/0010302 A1 1/2022 Mirkin et al.
2022/0056220 A1 2/2022 Mirkin et al.
2022/0175956 A1 6/2022 Mirkin et al.
2022/0288181 A1 9/2022 Mirkin et al.
2022/0288225 A1 9/2022 Wu
2022/0348985 A1 11/2022 Mirkin et al.
2022/0349005 A1 11/2022 Mirkin et al.
2022/0364095 A1 11/2022 Mirkin et al.
2022/0370490 A1 11/2022 Mirkin et al.
2022/0387585 A1 12/2022 Mirkin et al.
2023/0088835 A1 3/2023 Mirkin et al.
2023/0147733 A1 5/2023 Mirkin et al.

FOREIGN PATENT DOCUMENTS

CA 2651839 C 2/2016
CN 103212089 A 7/2013
CN 101484588 B 11/2013
EP 1072679 A2 1/2001
EP 2162117 A2 3/2010
EP 2399608 A1 12/2011
EP 2584047 B1 4/2013
ES 2392478 T3 12/2012
HK 1152529 3/2012
JP 5570806 B2 8/2014
KR 10-1734308 B1 5/2017
KR 10-1320916 B1 10/2023
WO 96/34876 A1 11/1996
WO 97/12896 A1 4/1997
WO 98/39352 A1 9/1998
WO 99/14226 A2 3/1999
WO 00/68248 A2 11/2000
WO 2001/062895 A2 8/2001
WO 02/96262 A2 12/2002
WO 03/86280 A2 10/2003
WO 2004/015075 A3 2/2004
WO 2005/063201 A2 7/2005
WO 2005/063288 A1 7/2005
WO 2006/138145 A1 12/2006
WO 2007/008463 A2 1/2007
WO 2007/064857 A2 6/2007
WO WO-2007076328 A2 * 7/2007 ........... A61K 31/713
WO 2007/096134 A1 8/2007
WO 2008/014979 A2 2/2008
WO 2008/042156 A1 4/2008
WO 2008/151022 A2 12/2008
WO 2008/151049 A2 12/2008
WO 2007/134161 A8 5/2009
WO 2009/061515 A1 5/2009
WO 2009/073984 A1 6/2009
WO 2009/120887 A2 10/2009
WO WO-2010060110 A1 * 5/2010 ........... A61K 31/713
WO 2010/105209 A1 9/2010
WO 2010/120420 A1 10/2010
WO 2011/008730 A3 1/2011
WO 2011/017456 A2 2/2011
WO 2011/028850 A1 3/2011
WO 2012/055933 A1 5/2012
WO 2012/068470 A2 5/2012
WO 2013/012628 A2 1/2013
WO 2013/028843 A1 2/2013
WO 2013/049941 A1 4/2013
WO 2013/151771 A1 10/2013
WO 2013/173693 A1 11/2013
WO 2014/169264 A2 10/2014
WO 2015/013673 A1 1/2015
WO 2015/013675 A1 1/2015
WO WO-2015126502 A2 * 8/2015 ............. A61K 48/00
WO 2015/187966 A1 12/2015
WO WO-2016004168 A1 * 1/2016 ......... A61K 31/7105
WO 2016/028940 A1 2/2016
WO 2016/081911 A2 5/2016
WO 2017/027468 A1 2/2017
WO 2017/031086 A1 2/2017
WO 2017/035278 A1 3/2017
WO 2017/136467 A1 8/2017
WO 2017/143156 A1 8/2017
WO 2018/022694 A1 2/2018
WO 2018/067302 A2 4/2018
WO 2018/152327 A1 8/2018
WO 2018/175445 A1 9/2018
WO 2018/209270 A1 11/2018
WO 2018/213585 A1 11/2018
WO 2019/032241 A1 2/2019
WO 2019/070890 A1 4/2019
WO 2019/118883 A1 6/2019
WO 2019/200262 A1 10/2019

(56) References Cited

FOREIGN PATENT DOCUMENTS

| | | | |
|---|---|---|---|
| WO | 2019/217870 | A1 | 11/2019 |
| WO | 2020/056341 | A2 | 3/2020 |
| WO | 2020/068905 | A1 | 4/2020 |
| WO | 2020/118259 | A1 | 6/2020 |
| WO | 2020/181144 | A1 | 9/2020 |
| WO | 2020/257674 | A1 | 12/2020 |
| WO | 2021/034956 | A2 | 2/2021 |
| WO | 2021/177996 | A1 | 9/2021 |
| WO | 2021/207630 | A1 | 10/2021 |
| WO | 2022/155149 | A1 | 7/2022 |
| WO | 2022/183043 | A1 | 9/2022 |
| WO | 2022/192038 | A1 | 9/2022 |
| WO | 2022/204427 | A1 | 9/2022 |
| WO | 2022/212564 | A1 | 10/2022 |
| WO | 2023/092040 | A1 | 5/2023 |
| WO | 2023/107389 | A1 | 6/2023 |

OTHER PUBLICATIONS

Pavlova et al., Amphiphilic "Like-a-Brush" Oligonucleotide Conjugates with Three Dodecyl Chains: Self-Assembly Features of Novel Scaffold Compounds for Nucleic Acids Delivery, Nanomaterials, 10(10):1948 (2020).
Peter et al., Characterization of suppressive oligodeoxynucleotides that inhibit Toll-like receptor-9-mediated activation of innate immunity, Immunology, 123(1):118-128 (2008).
Pettersen et al., UCSF Chimera-A visualization system for exploratory research and analysis, J. Comput. Chem., 25(13):1605-1612 (2004).
Pfeiffer et al., Bivalent Cholesterol-Based Coupling of Oligonucleotides to Lipid Membrane Assemblies, J. Am. Chem. Soc., 126:10224-10225 (2004).
Pfeiffer et al., Quantification of oligonucleotide modifications of small unilamellar lipid vesicles, Anal. Chem., 78:7493-7498 (2006).
Pieters et al., Natural supramolecular protein assemblies, Chem. Soc. Rev., 45(1):24-39 (2016).
Pollard et al., Cellular motility driven by assembly and disassembly of actin filaments, Cell., 112(4):453-465 (2003).
Polymeropoulos et al., 50th Anniversary Perspective: Polymers with Complex Architectures, Macromolecules, 50(4):1253-1290 (2017).
Potter et al., The opsonization of bentonite particles by gammaglobulin, Journal of immunology, 87:110-118 (1961).
Prats Alfonso et al., Cancer prognostics by direct detection of p53-antibodies on gold surfaces by impedance measurements, Small, 8:2106-15 (2012).
Prigodich et al., Nano-flares for mRNA regulation and detection, ACS Nano, 3(8):2147-2152 (2009).
Prigodich et al., Selective enhancement of nucleases by polyvalent DNA-functionalized gold nanoparticles, Journal of the American Chemical Society, 133(7):2120-2123 (2011).
Protozanova et al., Frank-Kamenetskii, M. D., Stacked-Unstacked Equilibrium at the Nick Site of DNA, J. Mol. Biol., 342(3):775-785 (2004).
Prozeller et al., Prevention of Dominant IgG Adsorption on N anocarriers in IgG-Enriched Blood Plasma by Clusterin Precoating, Advanced Science, 6(10):1802199 (2019).
Qin et al., Development of Spherical Nucleic Acids for Prostate Cancer Immunotherapy, Frontiers in Immunology, 11:1333 (2020).
Qu et al., Self-Assembled DNA Dendrimer Nanoparticle for Efficient Delivery of Immunostimulatory CpG Motifs. ACS Appl Mater Interfaces, 9(24):20324-20329 ( 2017).
Randeria et al., siRNA-based spherical nucleic acids reverse impaired wound healing in diabetic mice by ganglioside GM3 synthase knockdown, Proceedings of the National Academy of Sciences, 112(18):5573-5578 (2015).
Reddy et al., Exploiting lymphatic transport and complement activation in nanoparticle vaccines, Nat. Biotechnol., 25 (10):1159-1164 (2007).
Rennie et al., Auto-regulated Protein Assembly on a Supramolecular Scaffold, Angew. Chem., 130(42):13960-13965 (2018).
Resenbaum et al., GPCR Engineering Yields High-Resolution Structural Insights into ß2-Adrenergic Receptor Function, Science, 318:1266-1273 (2007).
Rincon-Restrepo et al., Vaccine nanocarriers: Coupling intracellular pathways and cellular biodistribution to control CD4 vs CD8 T cell responses, Biomaterials, 132:48-58 (2017).
Ritz et al., Protein Corona of Nanoparticles: Distinct Proteins Regulate the Cellular Uptake, Biomacromolecules, 16 (4):1311-1321 (2015).
Rohou et al., CTFFIND4: Fast and accurate defocus estimation from electron micrographs, Journal of Structural Biology, 192(2):216-221 (2015).
Rohs et al., Origins of Specificity in Protein-DNA Recognition, Annu. Rev. Biochem., 79:233-269 (2010).
Romberg et al., Sheddable coatings for long-circulating nanoparticles, Pharm. Res., 25(1):55-71 (2008).
Rosi et al., Nanostructures in biodiagnostics, Chem. Rev., 105(4): 1547-1562 (2005).
Rosi et al., Oligonucleotide-modified gold nanoparticles for intracellular gene regulation, Science, 312 (5776):1027-1030 (2006).
Rostovtsev et al., A stepwise huisgen cycloaddition process: copper(I)-catalyzed regioselective "Ligation" of azides and terminal alkynes†, Angewandte chemie, 114(14): 2708-2711 (2002).
Rothemund, Folding DNA to create nanoscale shapes and patterns, Nature, 440:297-302 (2006).
Ruan et al., DNA nanoclew templated spherical nucleic acids for siRNA delivery, Chemical Communications, 54(29):3609-3612 (2018).
Rye et al., Stable fluorescent complexes of double-stranded DNA with bis-intercalating asymmetric cyanine dyes: properties and applications, Nucleic Acids Res., 20(11):2803-2812 (1992).
Ryou et al., Delivery of shRNA using gold nanoparticle-DNA oligonucleotide conjugates as a universal carrier, Biochemical and Biophysical Research Communications, 398(3):542-546 (2010).
Saha et al., Regulation of Macrophage Recognition through the Interplay of Nanoparticle Surface Functionality and Protein Corona, ACS Nano, 10(4):4421-30 (2016).
Sakai et al., Protein crystalline frameworks with controllable interpenetration directed by dual supramolecular interactions, Nat. Commun., 5:4634 (2014).
Salvati et al., Transferrin-functionalized nanoparticles lose their targeting capabilities when a biomolecule corona adsorbs on the surface, Nat. Nanotechnol., 8:137-143 (2013).
Sambrook et al., Molecular Cloning: A Laboratory Manual, 2nd Edition, Cold Spring Harbor, New York (1989).
Sanger et al., DNA sequencing with chain-terminating inhibitors, Proc. Natl. Acad. Sci. USA, 74(12):5463-5467 (1977).
Sanghvi, Chapter 15, Antisense research and applications, Crooke, S.T. and Lebleu, B. ea., CRC Press, 289-302 (1993).
Schaffler et al., Blood protein coating of gold nanoparticles as potential tool for organ targeting, Biomaterials, 35 (10):3455-66 (2014).
Schoedel et al., Structures of Metal-Organic Frameworks with Rod Secondary Building Units, Chem. Rev., 116 (19):12466-12535 (2016).
Schottler et al., Protein adsorption is required for stealth effect of poly(ethylene glycol)- and poly(phosphoester)-coated nanocarriers, Nat. Nanotechnol., 11:372-377 (2016).
Schrittwieser et al., Biocatalytic Cascade for the Synthesis of Enantiopure ß-Azidoalcohols and ß-Hydroxynitriles, Eur. J. Org. Chem., 2009(14):2293-2298 (2009).
Schrodinger, The PyMOL Molecular Graphics System, Version 1.8, (2015).
Schroit et al., Liposome-cell interactions: in vitro discrimination of uptake mechanism and in vivo targeting strategies to mononuclear phagocytes, Chemistry and physics of lipids, 40:373-393 (1986).
Schuurmann et al., External validation and prediction employing the predictive squared correlation coefficient test set activity mean vs training set activity mean, Journal of chemical information and modeling, 48(11):2140-2145 (2008).
Seeman et al., Nucleic acid junctions and lattices, J. Theor. Biol., 99(2):237-247 (1982).

(56) References Cited

OTHER PUBLICATIONS

A Study of AST-008 in Healthy Subjects, ClinicalTrials.gov Identifier: NCT03086278, Mar. 22, 2017.
Adlakha-Hutcheon et al., Controlled destabilization of a liposomal drug delivery system enhances mitoxantrone antitumor activity, Nat. Biotechnol., 17(8):775-779 (1999).
Agbasi-Porter et al., Transcription inhibition using oligonucleotide-modified gold nanoparticles, Bioconiugate Chem., 17(5):1178-83 (2006).
Agren et al., Cytokine responses to CpG DNA in human leukocytes, Scand. J. Immunol., 64(1):61-8 (2006).
Aguilera et al., Systemic in vivo distribution of activatable cell penetrating peptides is superior to that of cell penetrating peptides, Integrative Biology, 1(5-6):371-381 (2009).
Ahmadi et al., Shape-Controlled Synthesis of Colloidal Platinum Nanoparticles, Science, 272(5270):1924-6 (1996).
Ahmed et al., Human serum albumin-based probes for molecular targeting of macrophage scavenger receptors, International journal of nanomedicine, 14:3723-3741 (2019).
Aida et al., Functional Supramolecular Polymers, Science, 335(6070):813-817 (2012).
Akinc et al., A combinatorial library of lipid-like materials for delivery of RNAi therapeutics, Nat. Biotechnol., 26 (5):561-569 (2008).
Aktas et al., Relationship between CD107a expression and cytotoxic activity, Cell Immunol., 254(2):149-154 (2009).
Alemdaroglu et al., DNA block copolymer micelles—A combinatorial tool for cancer tanotechnology, Advanced materials, 20:899 (2008).
Alex et al., Phosphonated Calixarene as a “Molecular Glue” for Protein Crystallization, Cryst. Growth Des., 18 (4):2467-2473 (2018).
Ali et al., Vaccines combined with immune checkpoint antibodies promote cytotoxic T-cell activity and tumor eradication, Cancer Immunology Research, 4(2):95-100 (2016).
Altschul et al., Basic local alignment search tool, J. Mol. Biol., 215(3):403-410 (1990).
Anderson et al., Semi-automated synthesis and screening of a large library of degradable cationic polymers for gene delivery, Angewandte Chemie (International ed. in English), 42(27):3153-3158 (2003).
Andrews et al., Conjugation of lipid and CpG-containing oligonucleotide yields an efficient method for liposome incorporation, bioconjugate Chem., 22:1279-1286 (2011).
Aoyama et al., Clusterin in the protein corona plays a key role in the stealth effect of nanoparticles against phagocytes, Biochem Biophys Res. Commun., 480(4):690-695 (2016).
Arpino et al., Crystal Structure of Enhanced Green Fluorescent Protein to 1.35 Å Resolution Reveals Alternative Conformations for Glu222, PLoS One, 7(10):e47132 (2012).
Artzi et al., Cellulosomes: bacterial nanomachines for dismantling plant polysaccharides, Nat. Rev. Micro., 15 (2):83-95 (2016).
Bae et al., Targeted drug delivery to tumors: myths, reality and possibility, J. Control Release, 153(3)1198-205 (2011).
Bahncmann, in Photochemical Conversion and Storage of Solar Energy, eds. Pelizetti and Schiavello, 251 (1991).
Ban et al., Discovery of glycosyltransferases using carbohydrate arrays and mass spectrometry, Nat. Chem. Biol., 8:769-73 (2012).
Ban et al., On-chip synthesis and label-free assays of oligosaccharide arrays, Angew. Chem. Int. Ed. Eng., 47:3396-9 (2008).
Banchelli et al., Phospholipid membranes decorated by cholesterol-based oligonucleotides as soft hybrid nanostructures, J. Phys. Chem. B., 112:10942-10952 (2008).
Banga et al., Cross-linked micellar spherical nucleic acids from thermoresponsive templates, J. Am. Chem. Soc., (2017).
Banga et al., Liposomal spherical nucleic acids, J. Am. Chem. Soc., 136(28):9866-9 (2014).
Barnaby et al., Design Considerations for RNA Spherical Nucleic Acids (SNAs), Biocon. Chem., 27(9):2124-2131 (2016).
Barnaby et al., Probing the inherent stability of siRNA immobilized on nanoparticle constructs, Proceedings of the National Academy of Sciences, 111(27): 9739-9744 (May 21, 2014).
Battye et al., iMOSFLM: a new graphical interface for diffraction-image processing with MOSFLM, Acta Crystallogr., D67:271-281 (2011).
Baumann et al., Ionic effects on the elasticity of single DNA molecules, PNAS, 94(12):6185-6190 (1997).
Berman et al., The Protein Data Bank, Nucleic Acids Res., 28(1):235-242 (2000).
Bernardinelli et al., Entirely enzymatic nanofabrication of DNA-protein conjugates, Nucleic Acids Research, 45 (18):e160 (2017).
Berns et al., Cellular Assays with a Molecular Endpoint Measured by SAMDI Mass Spectrometry, Small, 12 (28):3811-3818 (2016).
Biswas et al., A tubular biocontainer: metal ion-induced 1D assembly of a molecularly engineered chaperonin, J. Am. Chem. Soc., 131(22):7556-7557 (2009).
Blanco et al., Principles of nanoparticle design for overcoming biological barriers to drug delivery, Nature biotechnology, 33:941-951 (2015).
Bobo et al., Nanoparticle-Based Medicines: A Review of FDA-Approved Materials and Clinical Trials to Date, Pharmaceutical research, 33:2373-2387 (2016).
Bouderault et al., Nanoscale tools to selectively destroy cancer cells, chem. Commun., (18):2118-2120 (2008).
Bousmail et al., Precision spherical nucleic acids for delivery of anticancer drugs, Chemical Science, 8:6218-6229 (2017).
Boutros et al., Safety profiles of anti-CTLA-4 and anti-PD-1 antibodies alone and in combination, Nature Reviews Clinical Oncology, 13:473-486 (2016).
Briley et al., In Nanomaterials for Biomedicine; American Chemical Society, 1119:1-20 (2012).
Brodin et al., DNA-Mediated Cellular Delivery of Functional Enzymes, J. Am. Chem. Soc., 137(47):14838-14841 (2015).
Brodin et al., DNA-mediated engineering of multicomponent enzyme crystals, Proc. Natl. Acad. Sci. U.S.A., 112 (15):4564-4569 (2015).
Brodin et al., Metal-directed, chemically tunable assembly of one-, two- and three-dimensional crystalline protein arrays, Nat. Chem., 4(5):375-82 (2012).
Bruggink et al., Concepts of Nature in Organic Synthesis:? Cascade Catalysis and Multistep Conversions in Concert, Org. Proc. Res. Dev., 7(5):622-640 (2003).
Brunette et al., Exploring the repeat protein universe through computational protein design, Nature, 528:580-584 (2015).
Brunetti et al., Nanoparticle-cored dendrimers: functional hybrid nanocomposites as a new platform for drug delivery systems, Nanoscale, 7: 3808-3816 (2015).
Brus, Quantum crystallites and nonlinear optics, Appl. Phys. A., 53, 465-474 (1991).
Bulbake et al., Liposomal Formulations in Clinical Use: An Updated Review, Pharmaceutics, 9(2):12 (2017).
Bunge et al., Lipophilic oligonucleotides spontaneously insert into lipid membranes, bind complementary DNA strands, and sequester into lipid-disordered domains, Langmuir, Mar. 17, 2007, vol. 23, No. 8, pp. 4455-4464.
Burgess, Liposome preparation—Avanti(Registered) Polar Lipids, Sigma-Aldrich, 3 pages (1998).
Seeman, DNA in a material world, Nature, 421:427-431 (2003).
Seferos et al., Locked nucleic acid-nanoparticle conjugates, ChemBioChem, 8:1230-1232 (2007).
Seferos et al., Nano-flares: Probes for Transfection and mRNA Detection in Living Cells, Journal of the American Chemical Society, 129(50):15477-15479 (2007).
Seferos et al., Polyvalent DNA Nanoparticle Conjugates Stabilize Nucleic Acids, Nano Letters, 9(1):308-311 (2009).
Senior et al., Stability of small unilamellar liposomes in serum and clearance from the circulation: the effect of the phospholipid and cholesterol components, Life Sci., 30:2123-2136 (1982).
Sentz et al., A Metal Organic Framework with Spherical Protein Nodes: Rational Chemical Design of 3D Protein Crystals, J. Am. Chem. Soc., 137(36):11598-11601 (2015).
Shchepinov et al., Oligonucleotide Dendrimers: From Polylabelled DNA Probes to Stable Nano-Structures, Nucleic Acids Research, 12(1):1-12 (1999).
Shchepinov et al., Oligonucleotide dendrimers: stable nano-structures, Nucleic Acids Research, 27(15):3035-3041 (1999).

(56) References Cited

OTHER PUBLICATIONS

Shchepinov et al., Oligonucleotide dendrimers: synthesis and use as polylabelled DNA probes, Nucleic Acids Res., 25(22):4447-4454 (1997).
Sijbesma et al., Reversible Polymers Formed from Self-Complementary Monomers Using Quadruple Hydrogen Bonding, Science, 278(5343):1601-1604 (1997).
Simoes et al., On the mechanisms of internalization and intracellular delivery mediated by pH-sensitive liposomes, Biochim Biophys Acta., 1515(1):23-37 (2001).
Simon et al., Exploiting the biomolecular corona: pre-coating of nanoparticles enables controlled cellular interactions, Nanoscale, 10(22):10731-10739 (2018).
Simon et al., Supercharging enables organized assembly of synthetic biomolecules, Nat. Chem., 11:204-212 (2019).
Skakuj et al., Conjugation Chemistry-Dependent T-Cell Activation with Spherical Nucleic Acids, Journal of the American Chemical Society, 140(4):1227-1230 (2018).
Slack et al., Rotaxane probes for protease detection by 129 Xe hyperCEST NMR, chemical communications, 53(6):1076-1079 (2017).
Small et al., Facilitating THP-1 macrophage studies by differentiating and investigating cell functions in polystyrene test tubes, Journal of Immunological Methods, 461:73-77 (2018).
Sobota et al., Binding of IgG-opsonized particles to FcyR is an active stage of phagocytosis that involves receptor clustering and phosphorylation, Journal of Immunology, 175(7):4450-4457 (2005).
Sokolova et al., The use of calcium phosphate nanoparticles encapsulating Toll-like receptor ligands and the antigen hemagglutinin to induce dendritic cell maturation and T cell activation, Biomaterials, 31:5627-5633 (2010).
Sparwasser et al., Bacterial DNA causes septic shock, Nature, 386(6623):336-337 (1997).
Sparwasser et al., Immunostimulatory CpG-oligodeoxynucleotides cause extramedullary murine hemopoiesis, J. Immunol., 162(4):2368-2374 (1999).
Sparwasser et al., Macrophages sense pathogens via DNA motifs: induction of tumor necrosis factor-alpha-mediated shock, Eur. J. Immunol., 27(7):1671-1679 (1997).
Sprangers et al., Liposomal spherical nucleic acids for regulating long noncoding RNAs in the nucleus, Small, 13 (10):10.1002/smll.201602753 (2016).
Staufenbiel et al., Targeting of Intravenous Polymeric Nanoparticles by Differential Protein Adsorption, Macromolecular Symposia, 345(1):42-50 (2014).
Stengel et al., Determinants for Membrane Fusion Induced by Cholesterol-Modified DNA Zippers, J. Phvs. Chem. B., 112:8264-74 (2008).
Stengel et al., DNA-Induced Programmable Fusion of Phospholipid Vesicles, J. Am. Chem. Soc., 129:9584-5 (2007).
Su et al., Assays of endogenous caspase activities: a comparison of mass spectrometry and fluorescence formats, Anal. Chem., 78(14):4945-4951 (2006).
Su et al., Using MALDI-TOF mass spectrometry to characterize interfacial reactions on self-assembled monolayers, Langmuir, 19:4867-70 (2003).
Su et al., Using mass spectrometry to characterize self-assembled monolayers presenting peptides, proteins, and carbohydrates, Angew. Chem. Int. Ed. Engl., 41:4715-8 (2002).
Subramanian et al., Self-Assembly of a Designed Nucleoprotein Architecture through Multimodal Interactions, ACS Cent. Sci., 4(11):1578-1586 (2018).
Sulkowski et al., The influence of temperature, cholesterol content and pH on liposome stability, J. Mol. Struct., 744-747:737-747 (2005).
Switaj et al., CpG Immunostimulatory Oligodeoxynucleotide 1826 Enhances Antitumor Effect of Interleukin 12 Gene-Modified Tumor Vaccine in a Melanoma Model in Mice, Clinical Cancer Research, 10:4165-4175 (2004).
Tarini et al., Ambient Occlusion and Edge Cueing for Enhancing Real Time Molecular Visualization, IEEE Trans. Vis. Comput. Graph., 12(5):1237-1244 (2006).
Thomas, The Interaction of HgCl2 with Sodium Thymonucleate, J. Am. Chem. Soc., 76(23):6032-6034 (1954).
Tincer et al., Immunostimulatory activity of polysccharidepoly (I:C) nanoparticles, Biomaterial., 32(18):4275-4282 (2011).
Tiwari et al., Drug delivery systems: An updated review, International journal of pharmaceutical investigation, 2(1):2-11 (2012).
Tondelli et al., Highly efficient cellular uptake of c-myb antisense oligonucleotides through specifically designed polymeric nanospheres, Nucl. Acids Res., 26(23):5425-5431 (1998).
Tonigold et al., Pre-adsorption of antibodies enables targeting of nanocarriers despite a biomolecular corona, Nat. Nanotechnol., 13(9):862-869 (2018).
Tsubery et al., Biochemical assays of immobilized oligonucleotides with mass spectrometry, Langmuir, 24:5433-8 (2008).
Tzeng et al., Temporally programmed CD8a+ DC activation enhances combination cancer immunotherapy, Cell reports, 17(10):2503-2511 (2016).
Uchida et al., Gallium arsenide nanocrystals prepared in quinoline, J. Phys. Chem., 95:5382-5384 (1992).
Usov et al., FiberApp: An Open-Source Software for Tracking and Analyzing Polymers, Filaments, Biomacromolecules, and Fibrous Objects, Macromolecules, 48(5):1269-1280 (2015).
Vafabakhsh et al., Extreme Bendability of DNA Less than 100 Base Pairs Long Revealed by Single-Molecule Cyclization, Science, 337(6098):1097-1101 (2012).
Vasher et al., Hairpin-like siRNA-Based Spherical Nucleic Acids, J. Am. Chem. Soc., 144:3174-3181 (2022).
Veiseh et al., Optical and MRI multifunctional nanoprobe for targeting gliomas, Nano Lett., 5(6):1003-1008 (2005).
Versluis et al., In situ modification of plain liposomes with lipidated coiled coil forming peptides induces membrane fusion, J. Am. Chem. Soc., 135:8057-8062 (2013).
Vuolanto et al., Development of Cross-Linked Antibody Fab Fragment Crystals for Enantioselective Separation of a Drug Enantiomer, Cryst. Growth Des., 3(5):777-782 (2003).
Wang et al., Altering DNA-Programmable Colloidal Crystallization Paths by Modulating Particle Repulsion, Nano Letters, 17:5126-32 (2017).
Wang et al., Controlled/“living” radical polymerization. atom transfer radical polymerization in the presence of transition-metal complexes, J. Am. Chem. Soc., 117(20):5614-5615 (1995).
Wang et al., Nanometer-sized semiconductor clusters: materials synthesis, quantum size effects, and photophysical properties, J. Phys. Chem., 95, 525-532 (1991).
Wang et al., Rational vaccinology with spherical nucleic acids, Proceedings of the National Academy of Sciences, 116(21):10473-10481 (2019).
Zheng et al., Topical delivery of siRNA-based spherical nucleic acid nanoparticle conjugates for gene regulation, Proceedings of the National Academy of Sciences, 109(30):11975-11980 (2012).
Zhu et al., Matrix metalloprotease 2-responsive multifunctional liposomal nanocarrier for enhanced tumor targeting, ACS Nano., 6(4):3491-3498 (2012).
Zimmermann et al., A novel silver(I)-mediated DNA base pair, J. Am. Chem. Soc., 124:13684-13685 (2002).
Bustamante et al., Entropic elasticity of lambda-phage DNA, Science, 265(5178):1599-1600 (1994).
Cagdas et al., Liposomes as potential drug carrier systems for drug delivery, In Application of Nanotechnology in Drug Delivery, Chapter 1, 51 pages (2014).
Cai et al., Recent Progress in Enzymatic Synthesis of Sugar Nucleotides, Carbohydr Res., 346(7):1576-1580 (2011).
Cai et al., The Crown and the Scepter: Roles of the Protein Corona in Nanomedicine, Adv Mater, 31(45):e1805740 (2019).
Calabrese et al., Biocompatible infinite-coordination-polymer nanoparticle-nucleic acid conjugates for antisense gene regulation, Angew. Chem. Int. Ed. Engl., 54(2):476-480 (2015).
Callmann et al., Impact of Liposomal Spherical Nucleic Acid Structure on Immunotherapeutic Function, ACS Cent. Sci.,.7(5):892-899 (2021).

(56) References Cited

OTHER PUBLICATIONS

Cao et al., Reversible cell-specific drug delivery with aptamer-functionalized liposomes, Angew. Chem. Int. Ed., 48:6494-6498 (2009).
Capaccioli et al., Cationic lipids improve antisense oligonucleotide uptake and prevent degradation in cultured cells and inhuman serum, Biochem. Biophys. Res. Commun., 197(2):818-825 (1993).
Carlson et al., Chemically Controlled Self-Assembly of Protein Nanorings, J. Am. Chem. Soc., 128(23):7630-7638 (2006).
Carothers, Polymerization, Chemical Reviews, 8(3):353-426 (1931).
Cedervall et al., Understanding the nanoparticle-protein corona using methods to quantify exchange rates and affinities of proteins for nanoparticles, Proceedings of the National Academy of Sciences, 104(7):2050-2055 (2007).
Chen et al., Dynamic protein assembly by programmable DNA strand displacement, Nat., 10:4 7 4-481 (2018).
Chen et al., XGBoost: A Scalable Tree Boosting System, Proceedings of the 22nd ACM SIGKDD International Conference on Knowledge Discovery and Data Mining, 785-794 (2016).
Cheng et al., Dendrimer-Based Lipid Nanoparticles Deliver Therapeutic FAH mRNA to Normalize Liver Function and Extend Survival in a Mouse Model of Hepatorenal Tyrosinemia Type I, Advanced Materials, 30(52):1-10(1805308) (2018).
Cheng et al., Nanoparticle Superlattices through Template-Encoded DNA Dendrimers, J. Am. Chem. Soc., 143:17170-17179 (2021).
Chien et al., DNA-nanoparticle micelles as supramolecular fluorogenic substrates enabling catalytic signal amplification and detection by DNAzyme probes, Chem. Commun., 47:167-169 (2011).
Chinen et al., Relationships between Poly(ethylene glycol) modifications on RNA-spherical nucleic acid conjugates and cellular uptake and circulation time, Bioconjugate Chemistry, 27(11):2715-2721 (2016).
Chinen et al., The Impact of Protein Corona Formation on the Macrophage Cellular Uptake and Biodistribution of Spherical Nucleic Acids, Small, 13(16):1603847 (2017).
Chinnathambi et al., Binding mode of CpG oligodeoxynucleotides to nanoparticles regulates bifurcated cytokine induction via Toll-like receptor 9, Scientific Reports, 2(534):1-9 (2012).
Cho et al., Targeted delivery of siRNA-generating DNA nanocassettes using multifunctional nanoparticles, Small 9 (11): 1964-1973 (2013).
Cho et al., Therapeutic nanoparticles for drug delivery in cancer, Clin. Cancer Res., 14(5)11310-1316 (2008).
Choi et al., Mechanism for the endocytosis of spherical nucleic acid nanoparticle conjugates, Proc. Natl. Acad. Sci. USA, 110(19):7625-30 (2013).
Chothia et al., Principles of protein-protein recognition, Nature, 256:705-708 (1975).
Chua et al., 3.9 Å structure of the nucleosome core particle determined by phase-plate cryo-EM, Nucleic Acids Res., 44(17):8013-8019 (2016).
Clercq et al., Interferon induction increased through chemical modification of a synthetic polyribonucleotide, Science, 165:1137-1139 (1969).
Cloutier et al., Spontaneous Sharp Bending of Double-Stranded DNA, Mol. Cell., 14(3):355-362 (2004).
Cohen-Hadar et al., Restructuring protein crystals porosity for biotemplating by chemical modification of lysine residues, Biotechnol. Bioeng., 108(1):1-11 (2011).
Cook, Medicinal chemistry of antisense oligonucleotides—future opportunities, Anti-Cancer Drug Design, 6:585-607 (1991).
Coulie et al., Tumour antigens recognized by T lymphocytes: at the core of cancer immunotherapy, Nature Reviews Cancer, 14(2):135-146 (2014).
Couvreur, Nanoparticles in drug delivery: past, present and future, Advanced drug delivery reviews, 65(1):21-23 (2013).
Curtis et al., A morphology-selective copper organosol, Angew. Chem. Int. Ed. Engl., 27, 1530-1533 (1988).
Cutler et al., Polyvalent nucleic acid nanostructures, J. Am. chem. Soc., 133(24)19254-9257 (2011).
Cutler et al., Polyvalent oligonucleotide iron oxide nanoparticle "click" conjugates, Nano Lett., 10(4)11477-1480 (2010).
Dai et al., Monoclonal Antibody-Functionalized Multilayered Particles: Targeting Cancer Cells in the Presence of Protein Coronas, ACS Nano, 9(3):2876-2885 (2015).
Daigneault et al., The Identification of Markers of Macrophage Differentiation in PMA-Stimulated THP-1 Cells and Monocyte-Derived Macrophages, Plos One, 5(1):e8668 (2010).
Danev et al., Volta potential phase plate for in-focus phase contrast transmission electron microscopy, PNAS, 111(44):15635-15640 (2014).
Dave et al., Programmable assembly of DNA-functionalized liposomes by DNA, ACS Nano, 5(2)11304-1312 (2011).
Demurtas et al., Bending modes of DNA directly addressed by cryo-electron microscopy of DNA minicircles, Nucleic Acids Res., 37(9):2882-2893 (2009).
Derewenda, Application of protein engineering to enhance crystallizability and improve crystal properties, Acta Crystallogr., D66:604-615 (2010).
Desai et al., Microtubule Polymerization Dynamics, Annu. Rev. Cell Dev. Biol., 13(1):83-117 (1997).
Desiraju, Crystal engineering: a holistic view, Angew. Chem. Int. Ed., 46(44):8342-8356 (2007).
Dillmore et al., A photochemical method for patterning the immobilization of ligands and cells to self-assembled monolayers, Langmuir, 20(17):7223-7231 (2004).
Ding et al., Gold Nanoparticles for Nucleic Acid Delivery, Mol. Ther., 22(6):1075-1083 (2014).
Dirks et al., Triggered amplification by hybridization chain reaction, PNAS, 101(43):15275-15278 (2004).
Distler et al., DNA Dendrons as Agents for Intracellular Delivery, J. Am. Chem. Soc., 143:13513-13518 (2021).
Docter et al., Quantitative profiling of the protein coronas that form around nanoparticles, Nature Protocols, 9:2030-2044 (2014).
Doyle et al., Rational design of a-helical tandem repeat proteins with closed architectures, Nature, 528:585-588 (2015).
Du et al., Kinking the double helix by bending deformation, Nucleic Acids Res., 36(4):1120-1128 (2008).
Dua et al., Liposomei Methods of Preparation and Applications, International Journal of Pharmaceutical Studies and Research, 3(2)114-20 (2012).
Durbin, Protein Crystallization, Annu. Rev. Phys. Chem., 47:171-204 (1996).
Weber et al., Nivolumab versus chemotherapy in patients with advanced melanoma who progressed after anti-CTLA-4 treatment (CheckMate 037): a randomised, controlled, open-label, phase 3 trial, The Lancet Oncology, 16:375-384 (2015).
Wei et al., Polyvalent Immunostimulatory Nanoagents with Self-Assembled CpG Oligonucleotide-Conjugated Gold Nanoparticles, Angewandte Chemie International Edition, 51(5):1202-1206 (2012).
Weller, Colloidal semiconductor Q-particles: Chemistry in the transition region between solid state and molecules, Angew. Chem. Int. Ed. Engl., 32, 41-53 (1993).
West et al., Recognition and signaling by toll-like receptors, Annu. Rev. Cell Dev. Biol., 22:409-37 (2006).
Whitehead et al., Knocking down barriers: advances in siRNA delivery, Nat. Rev. Drug. Discov., 8:129-138 (2009).
Willis et al., Liposome-Anchored Vascular Endothelial Growth Factor Aptamers, Bioconjugate Chem. 9 573-582 (1998).
Wilner et al., Enzyme cascades activated on topologically programmed DNA scaffolds, Nat. Nanotechnol., 4:249-254 (2009).
Wilson et al., pH-Responsive Nanoparticle Vaccines for Dual-Delivery of Antigens and Immunostimulatory Oligonucleotides, ACS Nano, 7(5):3912-3925 (2013).
Wing et al., Crystal structure analysis of a complete turn of B-DNA, Nature, 287:755-758 (1980).
Winn et al., Overview of the CCP4 suite and current developments, Acta Crystallogr., D67:235-242 (2011).
Winter, xia2: an expert system for macromolecular crystallography data reduction, J. Appl. Crystallogr., 43:186-190 (2010).
Wolters et al., Construction of a 42 base pair double stranded DNA microcircle, Nucleic Acids Res., 17 (13):5163-5172 (1989).

(56) References Cited

OTHER PUBLICATIONS

Wu et al., DNA aptamer-micelle as an efficient detection/delivery vehicle toward cancer cells, Proc. Natl. Acad. Sci. SA., 107(1):5-10 (2010).
Xing et al., Selective delivery of an anticancer drug with aptamer-functionalized liposomes to breast cancer cells in vitro and in vivo, J. Mater. Chem. B., 1:5288-5297 (2013).
Xu et al., Structure and Properties of DNA-Based Reversible Polymers, Macromolecules, 37(5):1863-1870 (2004).
Yaghi et al., Reticular synthesis and the design of new materials, Nature, 423:705-714 (2003).
Yamada et al., 'Crystal lattice engineering,' an approach to engineer protein crystal contacts by creating intermolecular symmetry: crystallization and structure determination of a mutant human RNase 1 with a hydrophobic interface of leucines, Protein Sci., 16(7):1389-1397 (2007).
Yamane et al., On the Complexing of Desoxyribonucleic Acid (DNA) by Mercuric Ion1, J. Am. Chem. Soc., 83 (12):2599-2607 (1961).
Yamankurt et al., Exploration of the nanomedicine-design space with high-throughput screening and machine learning, Nat. Biomed. Eng., 3(4):318-327 (2019).
Yamankurt et al., The effector mechanism of siRNA spherical nucleic acids, PNAS, 117(3):1312-1320 (2020).
Yan et al., Differential roles of the protein corona in the cellular uptake of nanoporous polymer particles by monocyte and macrophage cell lines, ACS Nano, 7(12):10960-70 (2013).
Yan et al., Localized Single-Stranded Bubble Mechanism for Cyclization of Short Double Helix DNA, Phys. Rev. Lett., 93(10):108108 (2004).
Yang et al., FRET Nanoflares for Intracellular mRNA Detection: Avoiding False Positive Signals and Minimizing Effects of System Fluctuations, Journal of the American Chemical Society, 137(26):8340-8343 (2015).
Yeo et al., Electroactive monolayer substrates that selectively release adherent cells, Chembiochem., 2:590-3 (2001).
Yeo et al., Electroactive substrates that reveal aldehyde groups for bio-immobilization, Adv Mater., 16:1352-6 (2004).
Yeo et al., Label-free detection of protein-protein interactions on biochips, Angew. Chem. Int. Ed. Engl., 44:5480-3 (2005).
Yeo et al., Self-assembled monolayers that transduce enzymatic activities to electrical signals, Angew. Chem. Int. Ed. Engl., 42:3121-4 (2003).
Yin et al., Supramolecular self-assembled nanoparticles mediate oral delivery of therapeutic TNF-? siRNA against systemic inflammation, Anaew. Chem. Int. Ed. Enal., 125(22):5757-5761 (2013).
Yonzon et al., A comparative analysis of localized and propagating surface plasmon resonance sensors: the binding of concanavalin a to a monosaccharide functionalized self-assembled monolayer, J. Am. Chem. Soc., 126:12669-76 (2004).
Young et al., Hollow spherical nucleic acids for intracellular gene regulation based upon biocompatible silica shells, Nano Lett., 12(7):3867-3871 (2012).
Yousaf et al., Biochemistry 39:1580-1580 (2000).
Yousaf et al., Diels-Alder Reaction for the selective immobilization of protein to electroactive self-assembled monolayers, J. Am. Chem. Soc., 121:4286-7 (1999).
Yousaf et al., The kinetic order of an interfacial diels-Alder Reaction depends on the environment of the immobilized dienophile, Angew. Chem. Int. Ed. Engl., 39:1943-6 (2000).
Yousaf et al., Turning on cell migration with electroactive substrates, Angew. Chem. Int. Ed. Engl., 40:1093-6 (2001).
Yousaf et al., Using electroactive substrates to pattern the attachment of two different cell populations, Proc. Natl. Acad. Sci. USA, 98:5992-6 (2001).
Yu et al., Accessible 5'-end of CpG-containing phosphorothioate oligodeoxynucleotides is essential for immunostimulatory activity, Bioorganic & medicinal chemistry letters, 10(23):2585-2588 (2000).
Yu et al., RNA interference by expression of short-interfering RNAs and hairpin RNAs in mammalian cells, Proceedings of the National Academy of Sciences, 99(9): 6047-6052 (Mar. 12, 2002).
Zhang et al., A general approach to DNA-programmable atom equivalents, Nat. Mater., 12(8)741-746 (2013).
Zhang et al., An extremely stable and orthogonal DNA base pair with a simplified three-carbon backbone, J. Am. Chem. Soc., 127:74-75 (2005).
Zhang et al., Antibody-linked Spherical Nucleic Acids for Cellular Targeting, Journal of the American Chemical Society, 134 (40):16488-16491 (2012).
Zhang et al., Informational Liposomes: Complexes Derived from Cholesteryl-conjugated Oligonucleotides and Liposomes, Tetrahedron Letters, 37(35):6243-6246 (1996).
Zhang et al., Inhibitory efficacy of hypoxia-inducible factor 1a short hairpin RNA plasmid DNA-loaded poly (D, L-lactide-co-glycolide) nanoparticles on choroidal neovascularization in a laser-induced rat model, Gene Therapy, 17: 338-351 (2010).
Zhang et al., PowerBLAST: a new network BLAST application for interactive or automated sequence analysis and annotation, Genome Res., 7(6):649-656 (1997).
Zhang et al., Strategy for Increasing Drug Solubility and Efficacy through Covalent Attachment to Polyvalent DNANanoparticle Conjugates, ACS Nano, 5(9):6962-6970 (2011).
Zhang et al., Structure-activity relationships of cationic shell-crosslinked knedel-like nanoparticles: shell composition and transfection efficiency/cytotoxicity, Biomaterials, 31:1805-1813 (2010).
Zhao et al., DNA Dendrimer-Streptavidin Nanocomplex: an Efficient Signal Amplifier for Construction of Biosensing Platforms, Anal Chem., 20;89(12):6907-6914 (2017).
Zhao et al., Effect of different chemically modified oligodeoxynucleotides on immune stimulation, Biochemical pharmacology, 51(2):173-182 (1996).
Zheng et al., A spherical nucleic acid platform based on self-assembled DNA biopolymer for high-performance cancer therapy, ACS Nano, 7(8):6545-6554 (2013).
Zheng et al., Aptamer nano-flares for molecular detection in living cells, Nano Lett., 9(9):3258-3261 (2009).
Zheng et al., MotionCor2: anisotropic correction of beam-induced motion for improved cryo-electron microscopy, Nature Methods, 14(4):331-332 (2017).
Li et al., Rapid evaluation and screening of interfacial reactions on self-assembled monolayers, Langmuir, 23:11826-35 (2007).
Li et al., Reversible and Chemically Programmable Micelle Assembly with DNA Block-Copolymer Amphiphiles, Nano Lett., 4(6): 1055-1058 (2004).
Li et al., Smart asymmetric vesicles with triggered availability of inner cell-penetrating shells for specific intracellular drug delivery, ACS Appl. Mater. Interfaces, 9(21):17727-17735 (2017).
Li et al., Steady-state of an enzymatic reaction is dependent on the density of reactant, Langmuir, 294-8 (2013).
Li et al., Synthesis of nanocrystals of Zr-based metal-organic frameworks with csq-net: significant enhancement in the degradation of a nerve agent simulant, Chem. Commun., 51(54):10925-10928 (2015).
Li et al., Thermal stability of DNA functionalized gold nanoparticles, Bioconjugate chem., 24:1790-1797 (2013).
Li Y, Tseng YD, Kwon SY, D'Espaux L, Bunch JS, McEuen PL, Luo D. Controlled assembly of dendrimer-like DNA. Nat Mater. Jan. 2004;3(1):38-42. doi: 10.1038/nmat1045. Epub Dec. 21, 2003. PMID: 14704783.
Li, Y. et al. Free cholesterol-loaded macrophages are an abundant source of tumor necrosis factor-alpha and interleukin-6: model of NF-kappaB- and map kinasedependent inflammation in advanced atherosclerosis, J. Biol. Chem., 280:21763-21772 (2005).
Liao et al., A spatially propagating biochemical reaction, Angew. Chem. Int. Ed. Engl., 50:706-8 (2011).
Liao et al., An adaptor domain-mediated autocatalytic interfacial kinase reaction, Chemistry, 15:12303-09 (2009).
Lin et al., Gold Nanoparticle Delivery of Modified CpG Stimulates Macrophases and Inhibits Tumor Growth for Enhanced Immunotherapy, Plos One, 8(5):e63550 (2013).

(56) References Cited

OTHER PUBLICATIONS

Liu et al., DNA-based micelles: synthesis, micellar properties and size-dependent cell permeability, Chemistry, 16:3791-3797 (2010).
Liu et al., Freezing directed construction of Bio/Nano interfaces: reagentless conjugation, Denser spherical nucleic acids, and better nanoflares, J. Am. Chem. Soc., 139(28): 9471-9474 (2017).
Liu et al., Membrane anchored immunostimulatory oligonucleotides for in vivo cell modification and localized immunotherapy, Angew. Chem. Int. Ed. Engl., 50(31):7052-7055 (2011).
Liu et al., New poly(d-glucaramidoamine)s Induce DNA nanoparticle formation and efficient gene delivery into mammalian cells, J. Am. Chem. Soc., 126:7422-7423 (2004).
Liu et al., Silica nanoparticle supported lipid bilayers for gene delivery, chem. Commun., 5100-5102 (2009).
Liu et al., Surface and Size Effects on Cell Interaction of Gold Nanoparticles with Both Phagocytic and Nonphagocytic Cells, Langmuir, 29(29):9138-9148 (2013).
Luk et al., Self-assembled monolayers of alkanethiolates presenting mannitol groups are inert to protein adsorption and cell attachment, Langmuir, 16:9604-8 (2000).
Luk et al., Stereochemical control of cell adhesion on self assembled monolayers presenting organized saccharides: Potential effects of templated water structure, Biochemistry, 42:8647 (2003).
Lundqvist et al., Nanoparticle size and surface properties determine the protein corona with possible implications for biological impacts, Proc. Natl. Acad. Sci. USA, 105(38):14265-70 (2008).
Luo et al., A STING-activating nanovaccine for cancer immunotherapy, Nature nanotechnology, 12:648-654 (2017).
Luo et al., MicroRNA-Catalyzed Cancer Therapeutics Based on DNA-Programmed Nanoparticle Complex, ACS Appl Mater Interfaces, 9(39):33624-33631 (2017).
Lv et al., Identification of a novel conserved HLA-A*0201-restricted epitope from the spike protein of SARS-CoV, BMC Immunology, 10:61 (2009).
Lytton-Jean et al., Highly Cooperative Behavior of Peptide Nucleic Acid Linked DNA Modified Gold Nanoparticle and Combo Polymer Aggregates, Advanced Materials, 21(6):706-709 (2009).
Macdonald et al., One-step site-specific modification of native proteins with 2-pyridinecarboxyaldehydes, Nat. Chem. Biol., 11(5):326-331 (2015).
Macfarlane et al., Nanoparticle Superlattice Engineering with DNA, Science, 334(6053):204-208 (2011).
Malam et al., Liposomes and nanoparticles: nanosized vehicles for drug delivery in cancer, Trends in pharmacological sciences, 30(11):592-599 (2009).
Mammadov et al., Virus-like nanostructures for tuning immune response, Sci. Rep., 5(16728):1-15 (2015).
Mandal et al., Rational drug design, Eur. J. Pharmacol., 625:90-100 (2009).
Mangsbo et al., Enhanced Tumor Eradication by Combining CTLA-4 or PD-1 Blockage with CpG Therapy, Journal of Immunotherapy, 33(3)1225-235 (2010).
Mann, Life as a nanoscale phenomenon, Angew. Chem. Int. Ed., 47(29):5306-5320 (2008).
Manson et al., Polyethylene glycol functionalized gold nanoparticles: the influence of capping density on stability in various media, Gold Bulletin, 44(2):99-105 (2011).
Marin et al., Functional assays of membrane-bound proteins with SAMDI-TOF mass spectrometry, Angew. Chem. Int. Ed. Engl., 46:8796-8 (2007).
Marinakos et al., Chem. Mater., 10:1214-1219 (1998).
Marinakos et al., Gold nanoparticles as templates for the synthesis of hollow nanometer-sized conductive polymer capsules, Adv. Mater., 11(1):34-37 (1999).
Marko et al., Stretching DNA, Macromolecules, 28(26):8759-8770 (1995).
Martin et al., A New Access to 2'-O-Alkylated Ribonucleosides and Properties of 2'-O-Alkylated Oliaoribonucleotides, Helv. Chim. Acta, 78(2):486-504 (1995).
Massart, Preparation of aqueous magnetic liquids in alkaline and acidic media, IEEE Transactions on Magnetics, 17, 1247-1248 (1981).
Massich et al., Regulating Immune Response Using Polyvalent Nucleic Acid-Gold Nanoparticle Conjugates, Molecular Pharmaceutics, 6(6):1934-1940 (2009).
Matijevic et al., Fine Particles Part II: Formation Mechanisms and Applications, MRS Bulletin, 16-47 (1990).
Mattiasson et al., Studies on a matrix-bound three-enzyme system, Biochim. Biophys. Acta., 235(1):253-257 (1971).
Mcallister et al., Polymeric nanogels produced via inverse microemulsion polymerization as potential gene and antisense delivery agents, J. Am. Chem. Soc., 124:15198-15207 (2002).
Mccluskie et al., CpG DNA as mucosal adjuvant, Vaccine, 18:231-237 (1999).
Mccoy et al., Phaser crystallographic software, J. Appl. Crystallogr., 40:658-674 (2007).
Mcmillan et al., DNA-Functionalized, Bivalent Proteins, J. Am. Chem. Soc., 140(22):6776-6779 (2018).
Mcmillan et al., Modulating Nanoparticle Superlattice Structure Using Proteins with Tunable Bond Distributions, J. Am. Chem. Soc., 139(5):1754-1757 (2017).
Mcmillan et al., Programming Protein Polymerization with DNA, J. Am. Chem. Soc., 140(46):15950-15956 (2018).
Mcmillan et al., Protein Materials Engineering with DNA, Acc. Chem. Res., 52(7):1939-1948 (2019).
Mcpherson et al., Introduction to protein crystallization, Acta Cryst., F70:2-20 (2014).
Mcpherson, Protein Crystallization. In Protein Crystallography: Methods and Protocols, (Springer New York), 17-50 (2017).
Eddaoudi et al., Modular Chemistry:? Secondary Building Units as a Basis for the Design of Highly Porous and Robust Metal-Organic Carboxylate Frameworks, Acc. Chem. Res., 34(4):319-330 (2001).
Elbakry et al., Layer-by-layer assembled gold nanoparticles for siRNA delivery, Nano Lett., 9(5):2059-64 (2009).
Eloy, J. O., de Souza, M. C., Petrilli, R., Barcellos, J.P. A, Lee, R. J., & Marchetti, J.M. (2014). Liposomes as carriers of hydrophilic small molecule drugs: strategies to enhance encapsulation and delivery. Colloids and surfaces B: Biointerfaces, 123, 345-363. (Year: 2014).
Emsley et al., Features and development of Coot, Acta Crystallogr., D66:486-501 (2010).
Engilberge et al., Tuning Protein Frameworks via Auxiliary Supramolecular Interactions, ACS Nano, 13 (9):10343-10350 (2019).
Englisch et al., Chemically modified oligonucleotides as probes and inhibitors, Angewandte Chemie, International Edition, 30:613-629 (1991).
Enustun et al., Coagulation of colloidal gold, J. Am. Chem. Soc., 85:3317-3328 (1963).
European Application No. 14883485, European Search Report and Opinion, mailed May 9, 2017.
Evans et al., How good are my data and what is the resolution?, Acta Crystallogr., D69:1204-1214 (2013).
Evans, An introduction to data reduction: space-group determination, scaling and intensity statistics, Acta Crystallogr., D67:282-292 (2011).
Evans, Scaling and assessment of data quality, Acta Crystallogr., D62:72-82 (2006).
Fang et al., Functionalized nanoparticles with long-term stability in biological media, Small, 5(14):1637-1641 (2009).
Farokhzad et al., Nanomedicine: developing smarter therapeutic and diagnostic modalities, Drug Delivery Rev., 58 (14):1456-1459 (2006).
Fattal et al., Biodegradable polyalkylcyanoacrylate nanoparticles for the delivery of oligonucleotides, J. Controlled Release, 53:137-143 (1998).
Feng et al., Covalent organic frameworks, Che. Soc. Rev., 41:6010-6022 (2012).
Feng et al., The synergy peptide PHSRN and the adhesion peptide RGD mediate cell adhesion through a common mechanism, Biochemistry, 43:15811-21 (2004).
Ferrari, Cancer nanotechnology: opportunities and challenges, Nature Reviews Cancer, 5:161-171 (2005).

(56) References Cited

OTHER PUBLICATIONS

Freier et al., The ups and downs of nucleic acid duplex stability: structure-stability studies on chemically-modified DNA:RNA duplexes, Nucleic Acids Research, 25(22):4429-4443 (1997).
Frens, Controlled Nucleation for the Regulation of the Particle Size in Monodisperse Gold Suspensions, Nature Physical Science, 241:20-22 (1973).
Frey et al., Bionanotechnology for vaccine design, Current opinion in biotechnology, 52:80-88 (2018).
Fu et al., Interenzyme Substrate Diffusion for an Enzyme Cascade Organized on Spatially Addressable DNA Nanostructures, J. Am. Chem. Soc., 134(12):5516-5519 (2012).
Fu et al., Multi-enzyme complexes on DNA scaffolds capable of substrate channelling with an artificial swinging arm, Nat. Nanotechnol., 9:531-536 (2014).
Fujimoto, Kenzo, Kenta Ishida, Li Xue, and Shigetaka Nakamura. "Effect of linker length on photo-cross-linking position mediated by click chemistry via [2+ 2] photocycloaddition." Photochemical & Photobiological Sciences 19, No. 6 (2020): 776-782.
Fujimoto, Kenzo. The Glen Report Newsletter, 12 pages, retrieved on Jun. 23, 2023 from https.//www.glenresearch.com/reports/gr30-24, face of document states: vol. 30.2, Dec. 2018.
Furumoto et al., Effect of coupling of albumin onto surface of PEG liposome on its in vivo disposition. International Journal of Pharmaceutics, 329(1-2):110-116 (2007).
Garcia-Alvarez et al., Kostarelos, K., In vivo formation of protein corona on gold nanoparticles. The effect of their size and shape, Nanoscale, 10(3):1256-1264 (2018).
Gawalt et al., A substituent effects study reveals the kinetic pathway for an interfacial reaction, J. Am. Chem. Soc., 126:15613-7 (2004).
Gendron et al., Vaccination with human papillomavirus type 16 E7 peptide with CpG oligonucleotides for prevention of tumor growth in mice, Archives of otolaryngology—head & neck surgery, 132(3)327-332 (2006).
Gentekos et al., Beyond Dispersity: Deterministic Control of Polymer Molecular Weight Distribution, J. Am. Chem. Soc., 138(6):1848-1851 (2016).
Gholarni et al., Controlled Assembly of SNAP-PNA-Fluorophore Systems on DNA Templates To Produce Fluorescence Resonance Energy Transfer, Bioconjug. Chem., 25(10):1820-1828 (2014).
Gibson et al., Enzymatic assembly of DNA molecules up to several hundred kilobases, Nat. Methods, 6(5):343-345 (2009).
Giljohann et al., Gene regulation with polyvalent siRNA-nanoparticle conjugates, J. Am. Chem. Soc., 131 (6):2072-2073 (2009).
Giljohann et al., Gold nanoparticles for biology and medicine, Angew. Chem. Int. Ed. Engl., 49(19):3280-3294 (2010).
Giljohann et al., Oligonucleotide loading determines cellular uptake of DNA-modified gold nanoparticles, Nano Letters, 7(12):3818-3821 (2007).
Gill et al., Calculation of protein extinction coefficients from amino acid sequence data, Anal. Biochem., 182 (2):319-326 (1989).
Gonen et al., Design of ordered two-dimensional arrays mediated by noncovalent protein-protein interfaces, Science, 348:1365-1368 (2015).
Grijalva et al., Oligonucleotide delivery: a patent review (2010-2013), Expert Opin. Ther. Pat., 24(7):801-819 (2014).
Grubbs et al., 50th Anniversary Perspective: Living Polymerization-Emphasizing the Molecule in Macromolecules, Macromolecules, 50(18):6979-6997 (2017).
Gu et al., Biomaterials and emerging anticancer therapeutics: engineering the microenvironment, Nature Reviews Cancer, 16:56-66 (2016).
Gulley et al., Avelumab (MSB0010718C), an anti-PD-L1 antibody, in advanced NSCLC patients: A phase 1b, open-label expansion trial in patients progressing after platinum-based chemotherapy, Journal of Clinical Oncology, 33 (15):8034-8034 (2015).
Gunnarsson et al., Liposome-based chemical barcodes for single molecule DNA detection using imaging mass soectrometry, Nano. Lett., 10:732-737 (2010).
Gunnarsson et al., Single-molecule detection and mismatch discrimination of unlabeled DNA targets, Nano Lett., 8:183-188 (2008).
Gurard-Levin et al., Combining mass spectrometry and peptide arrays to profile the specificities of histone deacetylases, Chembiochem., 10:2159-61 (2009).
Gurard-Levin et al., Combining self-assembled monolayers and mass spectrometry for applications in biochips, Annu. Rev. Anal. Chem., (Palo Alto Calif.) 1:767-800 (2008).
Gurard-Levin et al., High-throughput screening of small molecule libraries using SAMDI mass spectrometry, ACS Comb. Sci., 13:347-50 (2011).
Gurard-Levin et al., Peptide arrays identify isoform-selective substrates for profiling endogenous lysine deacetylase activity, ACS Chem. Biol., 5:863-73 (2010).
Gurard-Levin et al., The activity of HDAC8 depends on local and distal sequences of its peptide substrates, Biochemistry, 47:6242-50 (2008).
Hager et al., Tunable DNA Hybridization Enables Spatially and Temporally Controlled Surface-Anchoring of Biomolecular Cargo, Langmuir, 34:15021-15027 (2018).
Hatakeyama et al., Development of a novel systemic gene delivery system for cancer therapy with a tumor-specific cleavable PEG-lipid, Gene Ther., 14(1)68-77 (2006).
Hayashi, Ultrafine Particles, Vac. Sci. Technol. Jul./Aug. 1987, A5(4):1375-84 (1987).
Jiang et al., Tumor imaging by means of proteolytic activation of cell-penetrating peptides, Proc. Natl. Acad. Sci. U.S.A., 101(51):17867-17872 (2004).
Jones et al., Nanomaterials. Programmable materials and the nature of the DNA bond, Science, 347(6224):1260901 (2015).
Kandimalla et al., Conjugation of ligands at the 5'-end of CpG DNA affects immunostimulatory activity, Bioconjug Chem., 13(5):966-974 (2002).
Kandimalla et al., Secondary structures in CpG oligonucleotides affect immunostimulatory activity, Biochemical and Biophysical Research Communications, 306:948-953 (2003).
Kang et al., Noncovalent assembly. A rational strategy for the realization of chain-growth supramolecular polymerization, Science, 347(6222):646-651 (2015).
Kapadia et al., Spherical Nucleic Acid Nanoparticles: Therapeutic Potential, BioDrugs, 32:297-309 (2018).
Kashiwagi et al., Protein Nanotube Selectively Cleavable with DNA: Supramolecular Polymerization of "DNA-Appended Molecular Chaperones", J. Am. Chem. Soc., 140(1):26-29 (2018).
Kasuya et al., Bio-nanocapsule-liposome conjugates for in vivo pinpoint drug and gene delivery, Methods Enzymol., 464:147-166 (2009).
Kato et al., Biochemistry 40:8608-8608 (2001).
Kato et al., Rewiring cell adhesion, J. Am. Chem. Soc., 126:6504-5 (2004).
Katz et al., The reversible reaction of sodium thymonucleate and mercuric chloride, J. Am. Chem. Soc., 74:2238-2245 (1951).
Kawamoto et al., Enhanced Immunostimulatory Activity of Covalent DNA Dendrons, Chembiochem, 16;23 {4):e202100583 (2022).
Kelly et al., Targeted liposomal drug delivery to monocytes and macrophages, Journal of Drug Delivery, Article ID 727241:1-11 (2011).
Kelty et al., High-throughput synthesis and characterization of nanocrystalline porphyrinic zirconium metal-organic frameworks, Chem. Commun(Camb), 52(50):7854-7857 (2016).
Kemp et al., "Combo" nanomedicine: Co-delivery of multi-modal therapeutics for efficient, targeted, and safe cancer therapy, Advanced Drug Delivery Reviews, 98:3-18 (2016).
Khalaf et al., Cross-Linked Enzyme Crystals as Highly Active Catalysts in Organic Solvents, J. Am. Chem. Soc., 118(23):5494-5495 (1996).
Khalil et al., The future of cancer treatment: immunomodulation, CARs and combination immunotherapy, Nature reviews Clinical oncology, 13:273-290 (2016).
Khoshouei et al., Cryo-EM structure of haemoglobin at 3.2 A determined with the Volta phase plate, Nat. Commun., 8:16099 (2017).

(56) References Cited

OTHER PUBLICATIONS

Kim et al., Cationic solid lipid nanoparticles reconstituted from low density lipoprotein components for delivery of SiRNA, Mol. Pharm., 5(4):622-631 (2008).
Kim et al., Effect of bovine serum albumin on the stability of methotrexate-encapsulated liposomes, Arch. Pharmacal Res., 14:336-341 (1991).
Kim et al., Profiling the selectivity of DNA ligases in an array format with mass spectrometry, Nucleic Acids Res., 38:e2 (2010).
King et al., Accurate design of co-assembling multi-component protein nanomaterials, Nature, 510:103-108 (2014).
Koshy et al., Biomaterials for enhancing anti-cancer immunity, Current opinion in biotechnology, 40:1-8 (2016).
Kosturko et al., The crystal and molecular structure of a 2:1 complex of 1-methylthymine-mercury (II), Biochemistry, 13(19):3949-3952 (1974).
Kramer et al., Comparative Study of 5'- and 3'-Linked CpG-Antigen Conjugates for the Induction of Cellular Immune Responses, ACS Omega., 2(1):227-235 (2017).
Kramer et al., Intracellular Cleavable CpG Oligodeoxynucleotide-Antigen Conjugate Enhances Anti-tumor Immunity, Mol. Ther., 25(1):62-70 (2017).
Kreig, Toll-like receptor 9 (TLR9) agonists in the treatment of cancer, Oncogene, 27:116-167 (2008).
Krieg et al., CpG motifs in bacterial DNA trigger direct B-cell activation, Nature, 374:546-549 (1995).
Kroschwitz, The Concise Encyclopedia Of Polymer Science And Engineering, John Wiley & Sons, 858-859 (1990).
Kukowska-Latallo et al., Efficient transfer of genetic material into mammalian cells using Starburst polyamidoamine dendrimers, Proc. Natl. Acad. Sci. USA, 93:4897-4902 (1996).
Kulkarni et al., Mmp-9 responsive PEG cleavable nanovesicles for efficient delivery of chemotherapeutics to pancreatic cancer, Molecular Pharmaceutics, 11(7):2390-2399 (2014).
Kunzle et al., Binary Protein Crystals for the Assembly of Inorganic Nanoparticle Superlattices, J. Am. Chem. Soc., 138(39):12731-12734 (2016).
Kwon et al., Dependence of the rate of an interfacial Diels-Alder reaction on the steric environment of the immobilized dienophile:an example of enthalpy-entropy compensation, J. Am. Chem. Soc., 124:806-12 (2002).
Labib et al., Single-cell mRNA cytometry via sequence-specific nanoparticle clustering and trapping, Nature Chemistry, 10:489-495 (2018).
Lalonde et al., Cross-linked crystals of Candida rugosa lipase: highly efficient catalysts for the resolution of chiral esters, J. Am. Chem. Soc., 117(26):6845-6852 (1995).
Laouini et al., Preparation, characterization and applications of liposomes: state of the art, Journal of colloid science and biotechnology, 1:148-168 (2012).
Lawson et al., Solving the structure of human H ferritin by genetically engineering intermolecular crystal contacts, Nature, 349:541-544 (1991).
Lee et al., Imageable Antigen-Presenting Gold Nanoparticle Vaccines for Effective Cancer Immunotherapy In vivo, Angewandte Chemie International Edition, 51(35):8800-8805 (2012).
Lee et al., Induction of Potent Antigen-specific Cytotoxic T Cell Response by PLGA-nanoparticles Containing Antigen and TLR Agonist, Immunel. Netw., 13(1):30-33 (2013).
Lee et al., Protein nanoarrays generated by dip-pen nanolithography, Science, 295:1702-5 (2002).
Lee et al., Silver nanoparticle-oligonucleotide conjugates based on DNA with triple cyclic disulfide moieties, Nano Lett., 7(7):2112-2115 (2007).
Leibly et al., A Suite of Engineered GFP Molecules for Oligomeric Scaffolding, Structure, 23(9):1754-1768 (2015).
Lesieur et al., Size analysis and stability study of lipid vesicles by high-performance gel exclusion chromatography, turbidity, and dynamic light scattering, Analytical Biochemistry, 192(2):334-343 (1991).
Li et al., A review on phospholipids and their main applications in drug delivery systems, Asian Journal of Pharmaceutical Sciences, 10:81-98 (2015).
Li et al., Catalytic asymmetric dihydroxylation by gold colloids functionalized with self-assembled monolayers, Langmuir, 15:4957-9 (1999).
Li et al., Combination Delivery of Antigens and CpG by Lanthanides-Based Core-Shell Nanoparticles for Enhanced Immune Response and Dual-Mode Imaging, Advanced Healthcare Materials, 2(10):1309-1313 (2013).
Li et al., Materials based tumor immunotherapy vaccines, Current Opinion in Immunology, 25(2):238-245 (2013).
Li et al., Molecular spherical nucleic acids, PNAS, 115(17):4340-4344 (2018).
Li et al., Nucleolin-targeting liposomes guided by aptamer AS1411 for the delivery of siRNA for the treatment of malignant melanomas, Biomaterials, 35(12):3840-3850 (2014).
Li et al., Polymer- and lipid-based nanoparticle therapeutics for the treatment of liver diseases, Nano Today 5 (4):296-312 (2010).
Hayes et al., DNA-Encoded Protein Janus Nanoparticles, J. Am. Chem. Soc., 140(29):9269-9274 (2018).
He et al., Catalytic Molecular Imaging of MicroRNA in Living Cells by DNA-Programmed Nanoparticle Disassembly, Angewandte Chemie International Edition, 55(9):3073-3076 (2016).
Heikenwalder et al., Lymphoid follicle destruction and immunosuppression after repeated CpG oligodeoxynucleotide administration, Nat. Med., 10(2):187-192 (2004).
Hemmi et al., A Toll-like receptor recognizes bacterial DNA, Nature, 408:740-745 (2000).
Henglein et al., Absorption spectrum and some chemical reactions of colloidal platinum in aqueous solution, J. Phys. Chem., 99, 14129-14136 (1995).
Henglein, Mechanism of reactions on colloidal microelectrodes and size quantization effects, Top. Curr. Chem., 143, 113-180 (1988).
Henglein, Small-particle research: physicochemical properties of extremely small colloidal metal and semiconductor particles, Chem. Rev., 89, 1861-1873 (1989).
Hodneland et al., Design of self-assembled monolayers that release attached groups using applied electrical potentials, Langmuir, 13:6001-3 (1997).
Hodneland et al., Selective immobilization of proteins to self-assembled monolayers presenting active site-directed capture ligands, Proc. Natl. Acad. Sci. USA, 99:5048-52 (2002).
Hollingsworth, Crystal Engineering: from Structure to Function, Science, 295:2410-2413 (2002).
Hope et al., Generation of multilamellar and unilamellar phospholipid vesicles, Chemistry and Physics of Lipids, 40:89-107 (1986).
Hope et al., Production of large unilamellar vesicles by a rapid extrusion procedure: characterization of size distribution, trapped volume and ability to maintain a membrane potential, Biochim Biophys Acta, Jan. 10, 1985, vol. 812, No. 1, pp. 55-65.
Houot et al., T-cell modulation combined with intratumoral CpG cures lymphoma in a mouse model without the need for chemotherapy, Blood, 113(15):3546-3552 (2009).
Houseman et al., Carbohydrate arrays for the evaluation of protein binding and enzymatic modification, Chem. Biol., 9:443-54 (2002).
Houseman et al., Environment of Arg-Gly-Asp ligands influences the adhesion of fibroblasts to self-assembled monolayers, Cell Attachment to the Extracellular Matrix, p. 430a, Abstract 2494 (1998).
Houseman et al., Maleimide-functionalized self-assembled monolayers for the preparation of peptide and carbohydrate biochips, Langmuir, 19:1522-31 (2003).
Houseman et al., Model substrates for the dynamic control of cell behavior. Extracellular Matrix Cell Bahavior, p. 45a, Abstract 232 (2000).
Houseman et al., Model systems for studying polyvalent carbohydrate binding interactions, Top. Curr. Chem., 218:1-44 (2002).
Houseman et al., Peptide chips for the quantitative evaluation of protein kinase activity, Nat. Biotechnol., 20:270-4 (2002).
Houseman et al., The microenvironment of immobilized Arg-Gly-Asp peptides is an important determinant of cell adhesion, Biomaterials, 22:943-55 (2001).

(56) References Cited

OTHER PUBLICATIONS

Houseman et al., The role of ligand density in the enzymatic glycosylation of carbohydrates presented on self- assembled monolayers of alkanethiolates on gold, Angew. Chem. Int. Ed., 38:782-5 (1999).
Houseman et al., Towards quantitative assays with peptide chips:a surface engineering approach, Trends Biotechnol, 20:279-81 (2002).
Houseman et al., Using self-assembled monolayers that present Arg-Gly-Asp peptide ligands to study adhesion of fibroblasts, Extracellular Matrix-Cell Interaction, 11:p. A1095, Abstract 1395 (1997).
Humerickhouse et al., Characterization of CPT-11 hydrolysis by human liver carboxylesterase isoforms hCE-1 and hCE-2, Cancer Res., 60(5):1189-1192 (2000).
Hurst et al., Maximizing DNA loading on a range of gold nanoparticle sizes, Anal. chem., 78(24):8313-8318 (2006).
Hussain et al., A novel anionic dendrimer for improved cellular delivery of antisense oligonucleotides, Journal of Controlled Release, 99:139-155 (2004).
Immordino et al., Stealth liposomes: review of the basic science, rationale, and clinical applications, existing and potential, Int. J. Nanomedicine, 1(3):297-315 (2006).
International Application No. PCT/US18/65765, International Preliminary Report on Patentability, mailed Jun. 25, 2020.
International Application No. PCT/US18/65765, International Search Report and Written Opinion, mailed Mar. 14, 2019.
International Application No. PCT/US19/27229, International Preliminary Report on Patentability, mailed Oct. 22, 2020.
International Application No. PCT/US19/27229, International Search Report and Written Opinion, mailed Jul. 23, 2019.
International Application No. PCT/US19/51131, International Preliminary Report on Patentability, mailed Mar. 25, 2021.
International Application No. PCT/US19/51131, International Search Report and Written Opinion, mailed Feb. 27, 2020.
International Application No. PCT/US20/21275, International Preliminary Report on Patentability, mailed Sep. 16, 2021.
International Application No. PCT/US20/21275, International Search Report and Written Opinion, mailed Jul. 7, 2020.
International Application No. PCT/US2018/054221, International Preliminary Report on Patentability, mailed Apr. 16, 2020.
International Application No. PCT/US2018/054221, International Search Report and Written Opinion, mailed Dec. 26, 2018.
International Application No. PCT/US2019/065078, International Preliminary Report on Patentability, mailed Jun. 17, 2021.
International Application No. PCT/US2019/65078, International Search Report and Written Opinion, mailed Mar. 5, 2020.
International Preliminary Report on Patentability, United States Patent Office, PCT/US2014/068429, dated Jun. 7, 2016.
International Search Report and Written Opinion of the International Search Authority, United States Patent Office, PCT/US2014/068429, dated Aug. 10, 2015.
Intratumoral Cavrotolimod Combined With Pembrolizumab or Cemiplimab in Patients With Merkel Cell Carcinoma, Cutaneous Squamous Cell Carcinoma, or Other Advanced Solid Tumors, ClinicalTrials.gov ID, NCT03684785, 2022.
Irvine et al., Engineering synthetic vaccines using cues from natural immunity, Nature materials, 12:978-990 (2013).
Irvine et al., Synthetic nanoparticles for vaccines and immunotherapy, Chemical reviews, 115(19):11109-11146 (2015).
Jahn et al., Microfluidic directed formation of liposomes of controlled size, Langmuir, 23(11 ):6289-6293 (2007).
Jakobsen et al., Assembly of liposomes controlled by triple helix formation, Bioconjugate Chem., 24:1485-1495 (2013).
James et al., Subcellular curvature at the perimeter of micropatterned cells influences lamellipodial distribution and cell polarity, Cell Motil. Cytoskeleton., 65:841-52 (2008).
Jayaraman et al., Maximizing the potency of siRNA lipid nanoparticles for hepatic gene silencing in vivo, Angewandte Chemie International Edition, 51(23): 8529-8533 (2012).
Jensen et al., Spherical nucleic acid nanoparticle conjugates as an RNAi-based therapy for glioblastoma, Sci. Transl. Med., 5(209):209ra152-209ra152 (2013).
Jiang et al., Quantitative analysis of the protein corona on FePt nanoparticles formed by transferrin binding, Journal of the Royal Society, Interface, 7(Suppl 1):S5-S13 (2010).
Meckes et al., Enhancing the Stability and Immunomodulatory Activity of Liposomal Spherical Nucleic Acids through Lipid-Tail DNA Modifications, Small, 14(5):170290 (2018).
Menard, S. Applied Logistic Regression Analysis, 106 (Sage, 2002).
Meng HM, Zhang X, Lv Y, Zhao Z, Wang NN, Fu T, Fan H, Liang H, Qiu L, Zhu G, Tan W. DNA dendrimer: an efficient nanocarrier of functional nucleic acids for intracellular molecular sensing. ACS Nano. Jun. 24, 2014;8(6):6171-81. doi: 10.1021/nn5015962. Epub May 13, 2014. PMID: 24806614; PMCID: PMC4076030.
Mesmaeker et al., Backbone modifications in oligonucleotides and peptide nucleic acid systems, Current Opinion in Structural Biology, 5(3):343-355 (1995).
Mignani et al., Dendrimer-Enabled Therapeutic Antisense Delivery Systems as Innovation in Medicine, Bioconjugate Chemistry 30:1938-1950 (2019).
Min et al., A method for connecting solution-phase enzyme activity assays with immobilized format analysis by mass spectrometry, Anal. Chem., 76:3923-9 (2004).
Min et al., Peptide arrays: towards routine implementation, Curr. Opin. Chem. Biol., 8:554-8 (2004).
Min et al., Profiling kinase activities by using a peptide chip and mass spectrometry, Angew. Chem. Int. Ed. Engl., 43:5973-7 (2004).
Mirkin et al., A DNA-based method for rationally assembling nanoparticles into macroscopic materials, Nature, 382 (6592):607-609 (1996).
Mirshafiee et al., Impact of protein pre-coating on the protein corona composition and nanoparticle cellular uptake, Biomaterials, 75:295-304 (2016).
Mirshafiee et al., Protein corona significantly reduces active targeting yield, Chemical Communications, 49 (25):2557-2559 (2013).
Modica et al., Synthesis of Cyclic Megarnolecules, J. Am. Chem. Soc., 140(20):6391-6399 (2018).
Mohamed et al., Effect of toll-like receptor 7 and 9 targeted therapy to prevent the development of hepatocellular carcinoma, Liver Int., 35(3):1063-1076 (2015).
Mohamed et al., TLR9 mediates *S. aureus* killing inside osteoblasts via induction of oxidative stress, BMC Microbiology, 16(article 230):8 (2016).
Mohri et al., Self-assembling DNA dendrimer for effective delivery of immunostimulatory CpG DNA to immune cells, Biomacromolecules, 13;16(4):1095-1101 (2015).
Molina et al., Trastuzumab (Herceptin), a Humanized Anti-HER2 Receptor Monoclonal Antibody, Inhibits Basal and Activated HER2 Ectodomain Cleavage in Breast Cancer Cells, Cancer Research, 61(12):4744-4749 (2001).
Molino et al., Display of DNA on Nanoparticles for Targeting Antigen Presenting Cells, ACS Biomaterials Science & Engineering, 3(4):496-501 (2017).
Montavon et al., Three-component reaction discovery enabled by mass spectrometry of self-assembled monolayers, Nat. Chem., 4:45-51 (2012).
Moore et al., Introduction of soluble protein into the class I pathway of antigen processing and presentation, Cell, 54 (6):777-785 (1988).
Moreno, et al., Immunomodulatory spherical nucleic acids, PNAS, 112(13):3892-3897 (2015).
Moscariello et al., Brain Delivery of Multifunctional Dendrimer Protein Bioconjugates, Advanced Science, 5 (5):1-14(1700897) (2018).
Mou et al., Computational design of co-assembling protein-DNA nanowires, Nature, 525(7568):230-233 (2015).
Mrksich et al., Using self-assembled monolayers that present oligo(ethylene glycol) groups to control the interactions of proteins with surfaces, ACS Symp. Ser., 680:361-73 (1997).
Mrksich et al., Using self-assembled monolayers to understand the interactions of man-made surfaces with proteins and cells, Annu. Rev. Biophys. Biomol. Struct., 25:55-78 (1996).

(56) References Cited

OTHER PUBLICATIONS

Mrksich, A surface chemistry approach to studying cell adhesion, Chem. Soc. Rev., 29:267-73 (2000).
Mrksich, Dynamic substrates for cell biology, MRS Bull., 30:180-4 (2005).
Mrksich, Mass spectrometry of self-assembled monolayers:a new tool for molecular surface science, ACS Nano, 2:7-18 (2008).
Mrksich, Tailored substrates for studies of attached cell culture, Cell Mol. Life Sci., 54:653-62 (1998).
Mrksich, Using self-assembled monolayers to understand the biomaterials interface, Curr. Opin. Colloid Int. Sci., 2:83-8 (1997).
Mrksich, What can surface chemistry do for cell biology?, Curr. Opin. Chem. Biol., 6:794-7 (2002).
Murphy et al., Substrates for cell adhesion prepared via active site-directed immobilization of a protein domain, Langmuir, 20:1026-30 (2004).
Murshudov et al., REFMAC5 for the refinement of macromolecular crystal structures, Acta Crystallogr., D67:355-367 (2011).
Nagase, Substrate specificity of MMPs. In matrix metalloproteinase inhibitors in cancer therapy, Springer: 39-66 (2001).
Naidoo et al., Toxicities of the anti-PD-1 and anti-PD-L1 immune checkpoint antibodies, Annals of Oncology, 26 (12):2375-2391 (2015).
Nguyen et al., Enzyme-responsive nanoparticles for targeted accumulation and prolonged retention in heart tissue after myocardial infarction, Advanced Materials, 27(37):5547-5552 (2015).
Nguyen et al., Protein corona: a new approach for nanomedicine design, International journal of nanomedicine, 12:3137-3151 (2017).
Nielsen et al., Sequence-Selective Recognition of DNA by Strand Displacement with a Thymine-Substituted Polyamide, Science, 254:1497-1500 (1991).
Niemeyer et al., DNA-Directed Assembly of Bienzymic Complexes from In Vivo Biotinylated NAD(P)H:FMN Oxidoreductase and Luciferase, ChemBioChem, 3:242-245 (2002).
Nikolov et al., Bias-dependent admittance in hybrid bilayer membranes, Langmuir, 22(17):7156-7158 (2006).
Nogales, Structural Insights into Microtubule Function, Ann. Rev. Biochem., 69(1):277-302 (2000).
Nygren et al., The interactions between the fluorescent dye thiazole orange and DNA, Biopolymers, 46(1):39-51 (1998).
Ogawara et al., Pre-coating with serum albumin reduces receptor-mediated hepatic disposition of polystyrene nanosphere: implications for rational design of nanoparticles, Journal of Controlled Release, 100(3):451-455 (2004).
Ogi et al., Living supramolecular polymerization realized through a biomimetic approach, Nat. Chem., 6(3):188-95 (2014).
Ohayon et al., Designing Higher Resolution Self-Assembled 3D DNA Crystals via Strand Terminus Modifications, ACS Nano, 13(7):7957-7965 (2019).
Olshavsky et al., Organometallic synthesis of gallium-arsenide crystallites, exhibiting quantum confinement, J. Am. Chem. Soc., 112, 9438-9439 (1990).
Olson et al., Activatable cell penetrating peptides linked to nanoparticles as dual probes for in vivo fluorescence and MR imaging of proteases, Proceedings of the National Academy of Sciences, 107(9):4311-4316 (2010).
Otsuka et al., PEGylated nanoparticles for biological and pharmaceutical applications, Adv. Drug Delivery. Rev., 64:246-255 (2012).
Ozpolat et al., Nanomedicine based approaches for the delivery of siRNA in cancer, J. Intern. Med., 267(1):44-53 (2010).
Papapostolou et al., Engineering and exploiting protein assemblies in synthetic biology, Mol. Biosyst., 5 (7):723-732 (2009).
Park et al., DNA-programmable nanoparticle crystallization, Nature, 451:553-556 (2008).

* cited by examiner

Fig. 1

SEQUENCE LISTING

<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 1
gcucaucgcu cacaaccaau u 21

<210> SEQ ID NO 2
<211> LENGTH: 23
<212> TYPE: RNA
<213> ORGANISM: Artificial Sequence
<220> FEATURE:
<223> OTHER INFORMATION: Synthetic Polypeptide

<400> SEQUENCE: 2
aauugguugu gagcgaugag cac 23

HAIRPIN-LIKE OLIGONUCLEOTIDE-CONJUGATED SPHERICAL NUCLEIC ACID

CROSS-REFERENCE TO RELATED APPLICATIONS

This application is a U.S. National Phase of International Application No. PCT/US2020/021275, filed Mar. 5, 2020, which claims the priority benefit under 35 U.S.C. § 119 (e) of U.S. Provisional Patent Application No. 62/814,569, filed Mar. 6, 2019, which are incorporated herein by reference in their entirety.

STATEMENT OF GOVERNMENT SUPPORT

This invention was made with government support under U54CA199091-01 awarded by the National Institutes of Health. The government has certain rights in the invention.

FIELD OF THE INVENTION

The disclosure is generally related to oligonucleotides having a hairpin-like design, nanoparticles comprising the same, and methods of using the same.

BACKGROUND

Oligonucleotides such as small interfering RNA (siRNA) can silence expression of a targeted gene through RNA interference (RNAi), making it a promising tool for gene regulation therapy. siRNA-conjugated spherical nucleic acids (siRNA-SNAs), in which siRNA is radially arranged around a nanoparticle core, exhibit advantages over naked siRNA in terms of cellular uptake and resistance to nucleases; however, their current design poses limitations. For example, because only the passenger strand of the siRNA is conjugated to the nanoparticle core, the guide strand tends to dissociate during synthesis and during delivery to the target gene. Since the guide strand causes knockdown of the target gene, dissociation of the guide strand limits the therapeutic effect, wastes material, and introduces variability.

SUMMARY

In the hairpin-like oligonucleotide-spherical nucleic acid (SNA) design of the present disclosure, and in embodiments in which the oligonucleotide is siRNA, both the passenger and guide strands of the siRNA are components of a single hairpin-shaped siRNA molecule. The passenger strand and guide strand are connected by spacers and contain a moiety for attachment to the nanoparticle. The passenger and guide strands hybridize, forming a hairpin-like shape, and the attachment chemistry is used to conjugate the hairpin-like siRNA to the nanoparticle core in a radially-oriented fashion. The hairpin-like design virtually eliminates dissociation, leading to higher oligonucleotide loading per SNA, maximizes duplex efficiency, less wasted material, and better control of loading with lower variability.

Accordingly, in some aspects the disclosure provides a nanoparticle having a substantially spherical geometry comprising an oligonucleotide conjugated thereto (i.e., a spherical nucleic acid (SNA)), wherein the oligonucleotide comprises a structure as follows:

[nucleic acid sequence 1]—[linker]—[tethering agent]—[linker]$_y$—[nucleic acid sequence 2];

nucleic acid sequence 1 and nucleic acid sequence 2 are sufficiently complementary to hybridize to each other; x and y are each independently 0 or 1; the tethering agent comprises a moiety capable of covalently or non-covalently binding to the nanoparticle surface; and each linker is independently an oligomeric moiety comprising amino acids, a nucleic acid, a polymer, or a combination thereof. In some embodiments, nucleic acid sequence 1 and nucleic acid sequence 2 are each RNA. In some embodiments, nucleic acid sequence 1 has a free 5' end and nucleic acid sequence 2 has a free 3' end. In further embodiments, the polymer comprises ethylene glycol. In some embodiments, the polymer comprises Spacer-18 (18-O-Dimethoxytrityl-hexaethyleneglycol,1-[(2-cyanoethyl)-(N,N-diisopropyl)]-phosphoramidite). In some embodiments, the polymer comprises RNA. In some embodiments, the linker comprises RNA. In some embodiments, the linker comprises DNA. In some embodiments, x is 1. In some embodiments, the linker comprises two Spacer-18 moieties. In some embodiments, x is 0. In further embodiments, y is 1. In some embodiments, the linker comprises two Spacer-18 moieties. In still further embodiments, y is 0. In some embodiments, the tethering agent comprises a lipophilic group or a thiol. In some embodiments, the tethering agent comprises dithiol serinol. In some embodiments, the thiol bonds to a linker with a maleimide (for example and without limitation, succinimidyl 4-(p-maleimidophenyl)butyrate (SMPB)), which, in still further embodiments, bonds to a lipophilic group or other molecule for conjugation, such as a phospholipid (e.g., phosphatidylethanolamines). In some embodiments, the lipophilic group comprises tocopherol or cholesterol. In further embodiments, the cholesterol is cholesteryl-triethyleneglycol (cholesteryl-TEG). In some embodiments, tocopherol is chosen from the group consisting of a tocopherol derivative, alpha-tocopherol, beta-tocopherol, gamma-tocopherol and delta-tocopherol.

In some aspects, the disclosure provides a nanoparticle having a substantially spherical geometry comprising an oligonucleotide conjugated thereto, wherein the oligonucleotide comprises a structure as follows:

5'—[nucleic acid sequence 1]—3'—[Spacer-18 (hexaethyleneglycol)]$_2$—[dithiol serinol]—[Spacer-18 (hexaethyleneglycol)]$_2$—5'—[nucleic acid sequence 2]—3'; and nucleic acid sequence 1 and nucleic acid sequence 2 are sufficiently complementary to hybridize to each other.

In some embodiments, the nanoparticle comprises a plurality of lipid groups. In further embodiments, at least one lipid group is selected from the group consisting of the phosphatidylcholine, phosphatidylglycerol, and phosphatidylethanolamine family of lipids. In still further embodiments, at least one lipid group is 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1-oleoyl-2-hydroxy-sn-glycero-3-phosphoethanolamine, 1-stearoyl-2-hydroxy-sn-glycero-3-phosphoethanolamine, 1,2-distearoyl-sn-glycero-3-phosphoethanolamine, and 1,2-dielaidoyl-sn-glycero-3-phosphoethanolamine, 1,2-dioleoyl-sn-glycero-3-phosphoethanolamine-N-[azido(polyethylene glycol)] (DOPE-PEG-azide), 1,2-dioleoyl-sn-glycero-3-phosphoethanolamine-N-[maleimide (polyethylene glycol)] (DOPE-PEG-maleimide), 1,2-dipalmitoyl-sn-glycero-3-phosphoethanolamine-N-[azido (polyethylene glycol)] (DPPE-PEG-azide), 1,2-dipalmitoryl-sn-glycero-3-phosphoethanolamine-N-[maleimide(polyethylene glycol)] (DPPE-PEG-maleimide), 1,2-distearoyl-sn-glycero-3-phosphoethanolamine-N-[azido (polyethylene glycol)] (DSPE-PEG-azide), and 1,2-distearoyl-sn-glycero-3-phosphoethanolamine-N-[maleimide(polyethylene glycol)] (DSPE-PEG-maleimide), or 1,2-dihexadecanoyl-sn-glycero-3-phosphoethanolamine (DPPE).

In some embodiments, the nanoparticle is metallic. In further embodiments, the nanoparticle is a gold nanoparticle, a silver nanoparticle, a platinum nanoparticle, an aluminum nanoparticle, a palladium nanoparticle, a copper nanoparticle, a cobalt nanoparticle, an indium nanoparticle, or a nickel nanoparticle.

In further embodiments, the nanoparticle is composed of a polymer or polymers. In some embodiments, the polymer is poly (lactic-co-glycolic acid) (PLGA). PLGA nanoparticles are described in International Publication No. WO 2018/175445, incorporated herein by reference in its entirety. In some embodiments, the nanoparticle is an iron oxide nanoparticle.

In some embodiments, the diameter of the nanoparticle is less than or equal to about 100 nanometers, or less than or equal to about 50 nanometers, or less than or equal to about 40 nanometers. In further embodiments, the diameter of a SNA (which comprises a nanoparticle core plus oligonucleotides associated therewith) is less than or equal to about 200 nanometers, or less than or equal to about 100 nanometers. In some embodiments, the SNA comprises from about 10 to about 200 oligonucleotides. In some embodiments, the SNA comprises 85 oligonucleotides.

In some embodiments, the SNA further comprises an immunoregulatory oligonucleotide. In some embodiments, the immunoregulatory oligonucleotide modulates (i.e., upregulates or downregulates) activity of one or more Toll-like receptors (TLRs). In some embodiments, the immunoregulatory oligonucleotide comprises one or more CpG motifs. In some embodiments, the immunoregulatory oligonucleotide is a TLR7/8 agonist oligonucleotide. In some embodiments, the immunoregulatory oligonucleotide is a TLR9 agonist oligonucleotide.

In some aspects, the disclosure provides a method of inhibiting expression of a gene, comprising contacting a transcript of the gene with a SNA of the disclosure. In some embodiments, expression of said gene product is inhibited in vivo. In some embodiments, expression of said gene product is inhibited in vitro.

BRIEF DESCRIPTION OF THE FIGURES

FIG. 1 shows an example of hairpin-like siRNA.

DETAILED DESCRIPTION

Figure 2:
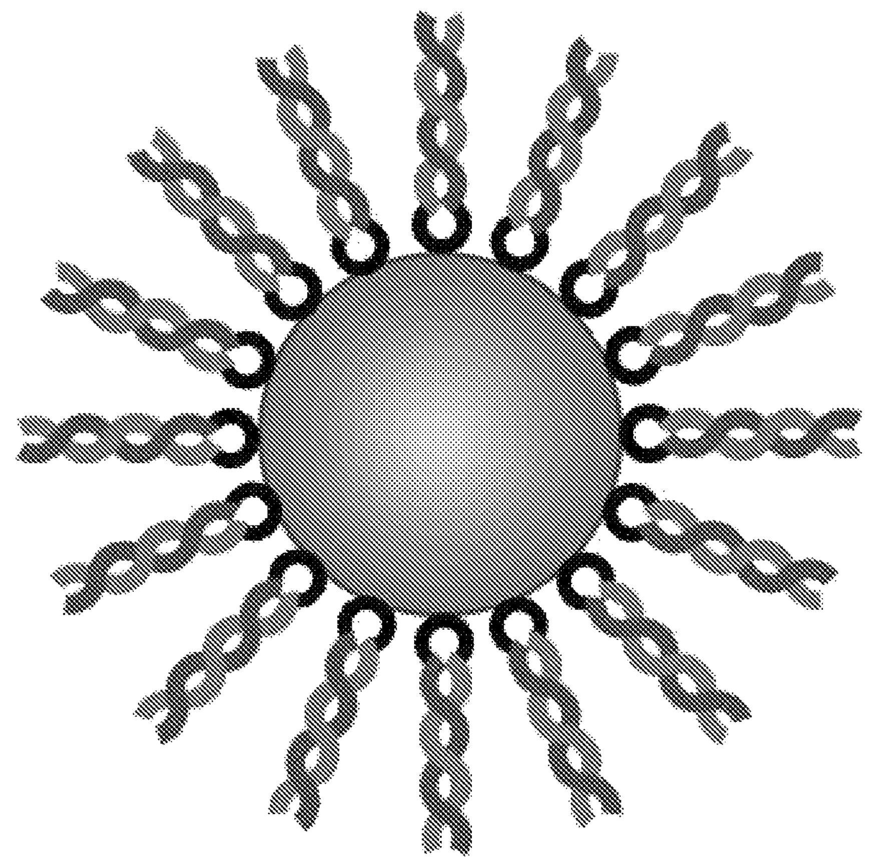
FIG. 2 depicts hairpin-like siRNA-SNA. Radial arrangement is shown in 2D for simplicity; in reality, hairpin-like siRNA is arranged radially around the spherical core in 3D.

As used in this specification and the appended claims, the singular forms "a," "an," and "the" include plural reference unless the context clearly dictates otherwise.

The terms "polynucleotide" and "oligonucleotide" are interchangeable as used herein.

The terms "conjugated," "attached," "functionalized," and "bound" are interchangeable as used herein and refer to the association of an oligonucleotide with a nanoparticle.

A "linker" as used herein is a moiety that joins a nucleic acid sequence to a tethering agent. In any of the aspects or embodiments of the disclosure, a linker is an oligomeric moiety comprising amino acids, a nucleic acid, a polymer, or a combination thereof.

A "tethering agent" as used herein is a moiety through which an oligonucleotide is attached to a nanoparticle.

Spherical Nucleic Acids. Spherical nucleic acids (SNAs) comprise densely functionalized and highly oriented polynucleotides on the surface of a nanoparticle which can either be organic (e.g., a liposome), inorganic (e.g., gold, silver, or platinum), or hollow (e.g., silica-based). The spherical architecture of the polynucleotide shell confers unique advantages over traditional nucleic acid delivery methods, including entry into nearly all cells independent of transfection agents and resistance to nuclease degradation. Furthermore, SNAs can penetrate biological barriers, including the blood-brain (see, e.g., U.S. Patent Application Publication No. 2015/0031745, incorporated by reference herein in its entirety) and blood-tumor barriers as well as the epidermis (see, e.g., U.S. Patent Application Publication No. 2010/0233270, incorporated by reference herein in its entirety).

Nanoparticles are therefore provided which are functionalized to have a polynucleotide attached thereto. In general, nanoparticles contemplated include any compound or substance with a high loading capacity for a polynucleotide as described herein, including for example and without limitation, a metal, a semiconductor, a liposomal particle, a polymer-based particle (e.g., a poly (lactic-co-glycolic acid) (PLGA) particle), insulator particle compositions, and a dendrimer (organic versus inorganic).

Thus, nanoparticles are contemplated which comprise a variety of inorganic materials including, but not limited to, metals, semi-conductor materials or ceramics as described in U.S. Patent Publication No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g., polypeptides such as BSA, polysaccharides, etc.), other biological materials (e.g., carbohydrates), and/or polymeric compounds are also contemplated for use in producing nanoparticles.

Liposomal particles, for example as disclosed in International Patent Application No. PCT/US2014/068429 (incorporated by reference herein in its entirety, particularly with respect to the discussion of liposomal particles) are also contemplated by the disclosure. Hollow particles, for example as described in U.S. Patent Publication Number 2012/0282186 (incorporated by reference herein in its entirety) are also contemplated herein. Liposomal particles of the disclosure have at least a substantially spherical geometry, an internal side and an external side, and comprise a lipid bilayer. The lipid bilayer comprises, in various embodiments, a lipid from the phosphocholine family of lipids or the phosphoethanolamine family of lipids. While not meant to be limiting, the first-lipid is chosen from group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), cardiolipin, lipid A, and a combination thereof.

In some embodiments, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe^{+4}$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992). In some embodiments, the nanoparticle is an iron oxide nanoparticle.

In practice, methods of increasing cellular uptake and inhibiting gene expression are provided using any suitable particle having oligonucleotides attached thereto that do not interfere with complex formation, i.e., hybridization to a target polynucleotide. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002, and International Application No. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Suitable nanoparticles are also commercially available from, for example, Ted Pella, Inc. (gold), Amersham Corporation (gold) and Nanoprobes, Inc. (gold).

Also as described in US Patent Publication No. 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in U.S. Patent Publication No. 20030147966, nanoparticles contemplated are produced using $HAuCl_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein. In further embodiments, a plurality of SNAs (e.g., liposomal particles) is produced and the SNAs in the plurality have a mean diameter of less than or equal to about 100 nanometers (e.g., about 5 nanometers to about 100 nanometers), or less than or equal to about 50 nanometers (e.g., about 5 nanometers to about 50 nanometers, or about 5 nanometers to about 40 nanometers, or about 5 nanometers to about 30 nanometers, or about 5 nanometers to about 20 nanometers, or about 10 nanometers to about 50 nanometers, or about 10 nanometers to about 40 nanometers, or about 10 nanometers to about 30 nanometers, or about 10 nanometers to about 20 nanometers). In further embodiments, the SNAs in the plurality created by a method of the disclosure have a mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers, or less than or equal to about 50 nanometers, or less than or equal to about 55 nanometers, or less than or equal to about 60 nanometers.

Oligonucleotides. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

In any of the aspects or embodiments of the disclosure, and as described herein, a single oligonucleotide comprises two nucleic acid sequences that are sufficiently complementary to each other to form a duplex (i.e., a hairpin-like oligonucleotide). The hairpin-like oligonucleotide comprises the following structure:

[nucleic acid sequence 1]—[linker]—[tethering agent]—[linker]$_y$—[nucleic acid sequence 2];

nucleic acid sequence 1 and nucleic acid sequence 2 are sufficiently complementary to hybridize to each other;

x and y are each independently 0 or 1;

the tethering agent comprises a moiety capable of covalently or non-covalently binding to the nanoparticle surface; and each linker is independently an oligomeric moiety comprising amino acids, a nucleic acid, a polymer, or a combination thereof. In some embodiments, nucleic acid sequence 1 has a free 5' end and nucleic acid sequence 2 has a free 3' end. In some embodiments, nucleic acid sequence 1 has a free 5' end and nucleic acid sequence 2 has a free 5' end. In some embodiments, nucleic acid sequence 1 has a free 3' end and nucleic acid sequence 2 has a free 3' end. In some embodiments, nucleic acid sequence 1 has a free 3' end and nucleic acid sequence 2 has a free 5' end. In some embodiments, nucleic acid sequence 1 and nucleic acid sequence 2 are each from about 10 to about 40 nucleotides in length. In preferred embodiments, nucleic acid sequence 1 and nucleic acid sequence 2 are each from about 20 to about 30 nucleotides in length. In any of the aspects or embodiments of the disclosure, nucleic acid sequence 1 and nucleic acid sequence 2 are or are about the same length. In some embodiments, nucleic acid 1 and nucleic acid 2 are 100% complementary to each other, i.e., a perfect match, while in further embodiments, nucleic acid 1 and nucleic acid 2 are about or at least (meaning greater than or equal to) about 99% complementary to each other, about or at least about 95%, about or at least about 90%, about or at least about 85%, about or at least about 80%, about or at least about 75%, about or at least about 70%, about or at least about 65%, about or at least about 60%, about or at least about 55%, or about or at least about 50% complementary to each other. In various embodiments, nucleic acid sequence 1 and nucleic acid sequence 2 are each RNA. In further embodiments, nucleic acid sequence 1 and nucleic acid sequence 2 are each DNA. In some embodiments, nucleic acid sequence 1 is RNA and nucleic acid sequence 2 is DNA. In some embodiments, nucleic acid sequence 1 is DNA and nucleic acid sequence 2 is RNA. The polymer, in various embodiments, comprises ethylene glycol. In some embodiments, the polymer comprises Spacer-18. One of skill in the art understands that Spacer-18 refers to 18-O-Dimethoxytritylhexaethyleneglycol,1-[(2-cyanoethyl)-(N,N-diisopropyl)]-phosphoramidite and that when Spacer-18 is incorporated within an oligonucleotide it is hexaethylene glycol. In various embodiments, x is 1 or 0. As used herein, when x is 1 it means that the linker is present in the oligonucleotide structure and when x is zero (0) it means that the linker is absent from the oligonucleotide structure. Thus, when x is 1 it means that the linker is present in the oligonucleotide structure and the linker comprises one or more units of a oligomeric moiety as described herein. By way of example, when x is 1 the linker can comprise one, two, three, or four Spacer-18 moieties. When x is zero (0), it means that the linker is absent from the oligonucleotide structure and therefore nucleic acid sequence 1 is joined directly to the tethering agent. In various embodiments, y is 1 or 0. In general, when y is 1 it means that the linker is present in the oligonucleotide structure and when y is zero (0) it means that the linker is absent from the oligonucleotide structure. Thus, when y is 1 it means that the linker is present in the oligonucleotide structure and the linker comprises one or more units of a oligomeric moiety as described herein. By way of example, when y is 1 the linker can comprise one, two, three, or four Spacer-18 moieties. When y is zero (0) it means that the linker is absent from the oligonucleotide structure and therefore nucleic acid sequence 2 is joined directly to the tethering agent. In some embodiments, the linker comprises RNA. In further embodiments, the RNA is from about 5 to about 10 ribonucleotides or more in length. In some embodiments, the RNA is less than about 10 ribonucleotides in length. In still further embodiments, the RNA does not hybridize to nucleic acid sequence 1 or nucleic acid sequence 2 when nucleic acid sequence 1 is hybridized to nucleic acid sequence 2. In some embodiments, the linker comprises DNA. In further embodiments, the DNA is from about 5 to about 10 nucleotides or more in length. In some embodiments, the DNA is less than about 10 nucleotides in length. In still further embodiments, the DNA does not hybridize to nucleic acid sequence 1 or nucleic acid sequence 2 when nucleic acid sequence 1 is hybridized to nucleic acid sequence 2. In some embodiments, both x and y are 0. In some embodiments, the tethering agent comprises a lipophilic group or a thiol. In some embodiments, the tethering agent is a dithiol serinol group, which in some embodiments is produced from a dithiol serinol phosphoramidite (3-Dimethoxytrityloxy-2-(3-((R)-α-lipoamido)propanamido)propyl-1-O-(2-cyanoethyl)-(N,N-diisopropyl)-phosphoramidite). In some embodiments, the lipophilic group comprises tocopherol or cholesterol. In some embodiments, the cholesterol is cholesteryl-triethyleneglycol (cholesteryl-TEG). In some embodiments, tocopherol is chosen from the group consisting of a tocopherol derivative, alpha-tocopherol, beta-tocopherol, gamma-tocopherol and delta-tocopherol. In further embodiments, the nanoparticle comprises a plurality of lipid groups. In some embodiments, at least one lipid group is selected from the group consisting of the phosphatidylcholine, phosphatidylglycerol, and phosphatidylethanolamine family of lipids, or a combination thereof. In some embodiments, at least one lipid group is 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1-oleoyl-2-hydroxy-sn-glycero-3-phosphoethanolamine, 1-stearoyl-2-hydroxy-sn-glycero-3-phosphoethanolamine, 1,2-distearoyl-sn-glycero-3-phosphoethanolamine, and 1,2-dielaidoyl-sn-glycero-3-phosphoethanolamine, 1,2-dihexadecanoyl-sn-glycero-3-phosphoethanolamine (DPPE), 1,2-dioleoyl-sn-glycero-3-phosphoethanolamine-N-[azido (polyethylene glycol)] (DOPE-PEG-azide), 1,2-dioleoyl-sn-glycero-3-phosphoethanolamine-N-[maleimide(polyethylene glycol)] (DOPE-PEG-maleimide), 1,2-dipalmitoyl-sn-glycero-3-phosphoethanolamine-N-[azido(polyethylene glycol)] (DPPE-PEG-azide), 1,2-dipalmitoryl-sn-glycero-3-phosphoethanolamine-N-[maleimide(polyethylene glycol)] (DPPE-PEG-maleimide),1,2-distearoyl-sn-glycero-3-phosphoethanolamine-N-[azido(polyethylene glycol)] (DSPE-PEG-azide), and 1,2-distearoyl-sn-glycero-3-phosphoethanolamine-N-[maleimide (polyethylene glycol)] (DSPE-PEG-maleimide), or a combination thereof.

In some aspects, the disclosure provides a nanoparticle having a substantially spherical geometry comprising an oligonucleotide conjugated thereto, wherein the oligonucleotide comprises a structure as follows:

5'—[nucleic acid sequence 1]—3'—[Spacer-18 (hexaethyleneglycol)]$_2$—[dithiol serinol]—[Spacer-18 (hexaethyleneglycol)]$_2$—5'—[nucleic acid sequence 2]—3'; and nucleic acid sequence 1 and nucleic acid sequence 2 are sufficiently complementary to hybridize to each other. In some embodiments, nucleic acid sequence 1 and nucleic acid sequence 2 are each from about 10 to about 40 nucleotides in length. In preferred embodiments, nucleic acid sequence 1 and nucleic acid sequence 2 are each from about 20 to about 30 nucleotides in length. In any of the aspects or embodiments of the disclosure, nucleic acid sequence 1 and nucleic acid sequence 2 are about the same length. In some embodiments, nucleic acid 1 and nucleic acid 2 are 100% complementary to each other, i.e., a perfect match, while in further embodiments, nucleic acid 1 and nucleic acid 2 are about or at least (meaning greater than or equal to) about 99% complementary to each other, about or at least about 95%, about or at least about 90%, about or at least about 85%, about or at least about 80%, about or at least about 75%, about or at least about 70%, about or at least about 65%, about or at least about 60%, about or at least about 55%, or about or at least about 50% complementary to each other. In various embodiments, nucleic acid sequence 1 and nucleic acid sequence 2 are each RNA. In further embodiments, nucleic acid sequence 1 and nucleic acid sequence 2 are each DNA. In some embodiments, nucleic acid sequence 1 is RNA and nucleic acid sequence 2 is DNA. In some embodiments, nucleic acid sequence 1 is DNA and nucleic acid sequence 2 is RNA.

Nanoparticles provided that are functionalized with a polynucleotide, or a modified form thereof generally comprise a polynucleotide from about 5 nucleotides to about 100 nucleotides in length. More specifically, nanoparticles are functionalized with a polynucleotide that is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 125, about 150, about 175, about 200, about 250, about 300, about 350, about 400, about 450, about 500 or more nucleotides in length are contemplated. In any of the aspects or embodiments of the disclosure, when a single oligonucleotide comprises two or more nucleic acid sequences (e.g., nucleic acid sequence 1, nucleic acid sequence 2, a linker (when linker is a nucleic acid)), then the length of the oligonucleotide is the sum of the length of the two or more nucleic acid sequences, and the sum may be any of the foregoing lengths.

In some embodiments, the polynucleotide attached to a nanoparticle is DNA. When DNA is attached to the nanoparticle, the DNA is in some embodiments comprised of a sequence that is sufficiently complementary to a target region of a polynucleotide such that hybridization of the DNA polynucleotide attached to a nanoparticle and the target polynucleotide takes place, thereby associating the target polynucleotide to the nanoparticle. The DNA in various aspects is single stranded or double-stranded, as long as the double-stranded molecule also includes a single strand region that hybridizes to a single strand region of the target polynucleotide. In some aspects, hybridization of the polynucleotide functionalized on the nanoparticle can form a triplex structure with a double-stranded target polynucleotide. In another aspect, a triplex structure can be formed by hybridization of a double-stranded oligonucleotide functionalized on a nanoparticle to a single-stranded target polynucleotide. In some embodiments, the disclosure contemplates that a polynucleotide attached to a nanoparticle is RNA. The RNA can be either single-stranded or double-stranded (e.g., siRNA), so long as it is able to hybridize to a target polynucleotide.

In some aspects, multiple polynucleotides are functionalized to a nanoparticle. In various aspects, the multiple polynucleotides each have the same sequence, while in other aspects one or more polynucleotides have a different sequence. In further aspects, multiple polynucleotides are arranged in tandem and are separated by a spacer. Spacers are described in more detail herein below.

Polynucleotide attachment to a nanoparticle. Polynucleotides contemplated for use in the methods include those bound to the nanoparticle through any means (e.g., covalent or non-covalent attachment). Regardless of the means by which the polynucleotide is attached to the nanoparticle, attachment in various aspects is effected through a 5' linkage, a 3' linkage, some type of internal linkage, or any combination of these attachments. In some embodiments, the polynucleotide is covalently attached to a nanoparticle. In further embodiments, the polynucleotide is non-covalently attached to a nanoparticle. An oligonucleotide of the disclosure comprises, in various embodiments, an associative moiety selected from the group consisting of a tocopherol, a cholesterol moiety, DOPE-butamide-phenylmaleimido, and lyso-phosphoethanolamine-butamide-pneylmaleimido. See also U.S. Patent Application Publication No. 2016/0310425, incorporated by reference herein in its entirety.

Methods of attachment are known to those of ordinary skill in the art and are described in US Publication No. 2009/0209629, which is incorporated by reference herein in its entirety. Methods of attaching RNA to a nanoparticle are generally described in PCT/US2009/65822, which is incorporated by reference herein in its entirety. Methods of associating polynucleotides with a liposomal particle are described in PCT/US2014/068429, which is incorporated by reference herein in its entirety.

Spacers. In certain aspects, functionalized nanoparticles are contemplated which include those wherein an oligonucleotide is attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, an ethylglycol, or combinations thereof.

In certain aspects, the polynucleotide has a spacer through which it is covalently bound to the nanoparticles. These polynucleotides are the same polynucleotides as described above. As a result of the binding of the spacer to the nanoparticles, the polynucleotide is spaced away from the surface of the nanoparticles and is more accessible for hybridization with its target. In various embodiments, the length of the spacer is or is equivalent to at least about 5 nucleotides, 5-10 nucleotides, 10 nucleotides, 10-30 nucleotides, or even greater than 30 nucleotides. The spacer may have any sequence which does not interfere with the ability of the polynucleotides to become bound to the nanoparticles or to the target polynucleotide. In certain aspects, the bases of the polynucleotide spacer are all adenylic acids, all thymidylic acids, all cytidylic acids, all guanylic acids, all uridylic acids, or all some other modified base.

Nanoparticle surface density. A surface density adequate to make the nanoparticles stable and the conditions necessary to obtain it for a desired combination of nanoparticles and polynucleotides can be determined empirically. Generally, a surface density of at least about 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Alternatively, the density of polynucleotide on the surface of the SNA is measured by the number of polynucleotides on the surface of a SNA. As described herein, in any of the aspects or embodiments of the disclosure, one or more oligonucleotides on the surface of a nanoparticle is a single polynucleotide of the disclosure comprises two nucleic acid sequences that are sufficiently complementary to each other to form a duplex. With respect to the surface density of polynucleotides on the surface of a SNA of the disclosure, it is contemplated that a SNA as described herein comprises from about 1 to about 25,000 oligonucleotides on its surface. In various embodiments, a SNA comprises from about 10 to about 200, or from about 10 to about 190, or from about 10 to about 180, or from about 10 to about 170, or from about 10 to about 160, or from about 10 to about 150, or from about 10 to about 140, or from about 10 to about 130, or from about 10 to about 120, or from about 10 to about 110, or from about 10 to about 100, or from 10 to about 90, or from about 10 to about 80, or from about 10 to about 70, or from about 10 to about 60, or from about 10 to about 50, or from about 10 to about 40, or from about 10 to about 30, or from about 10 to about 20 oligonucleotides on its surface. In some embodiments, a SNA comprises from about 80 to about 140 oligonucleotides on its surface. In further embodiments, a SNA comprises at least about 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 polynucleotides on its surface. In further embodiments, a SNA consists of 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 polynucleotides on its surface. In some embodiments, a liposomal SNA (which may, in various embodiments, be about or less than about 100 nanometers in diameter or about or less than about 50 nanometers in diameter or about or less than about 40 nanometers in diameter or about or less than about 30 nanometers in diameter) comprises from about 10 to about 1,000 oligonucleotides or from about 10 to about 40 oligonucleotides on its surface. In further embodiments, an iron oxide SNA (which may, in various embodiments, be less than about 100 nanometers in diameter or less than about 15 nanometers in diameter) comprises about 10 to about 25,000 oligonucleotides on its surface. In some embodiments, a PLGA SNA comprises from about 10 to about 800 oligonucleotides on its surface.

Uses of SNAs in Gene Regulation/Therapy

As disclosed herein, it is contemplated that in any of the aspects or embodiments of the disclosure, a SNA as disclosed herein possesses the ability to regulate gene expression. Thus, in some embodiments, a SNA of the disclosure comprises an oligonucleotide having gene regulatory activity (e.g., inhibition of target gene expression or target cell recognition). In any of the aspects or embodiments of the disclosure, the oligonucleotide is a hairpin-like siRNA oligonucleotide. Accordingly, in some embodiments the disclosure provides methods for inhibiting gene product expression, and such methods include those wherein expression of a target gene product is inhibited by about or at least about 5%, about or at least about 10%, about or at least about 15%, about or at least about 20%, about or at least about 25%, about or at least about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% compared to gene product expression in the absence of a SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of SNA and a specific oligonucleotide.

In various aspects, the methods include use of an oligonucleotide which is 100% complementary to the target polynucleotide, i.e., a perfect match, while in other aspects, the oligonucleotide is about or at least (meaning greater than or equal to) about 95% complementary to the polynucleotide over the length of the oligonucleotide, about or at least about 90%, about or at least about 85%, about or at least about 80%, about or at least about 75%, about or at least about 70%, about or at least about 65%, about or at least about 60%, about or at least about 55%, about or at least about 50%, about or at least about 45%, about or at least about 40%, about or at least about 35%, about or at least about 30%, about or at least about 25%, about or at least about 20% complementary to the polynucleotide over the length of the oligonucleotide to the extent that the oligonucleotide is able to achieve the desired degree of inhibition of a target gene product. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an inhibitory oligonucleotide in which 18 of 20 nucleotides of the inhibitory oligonucleotide are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an inhibitory oligonucleotide with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Accordingly, methods of utilizing a SNA of the disclosure in gene regulation therapy are provided. This method comprises the step of hybridizing a polynucleotide encoding the gene with one or more oligonucleotides complementary to all or a portion of the polynucleotide, the oligonucleotide being the additional oligonucleotide of a composition as described herein, wherein hybridizing between the polynucleotide and the additional oligonucleotide occurs over a length of the polynucleotide with a degree of complementarity sufficient to inhibit expression of the gene product. The inhibition of gene expression may occur in vivo or in vitro.

The oligonucleotide utilized in the methods of the disclosure is either RNA or DNA. The RNA can be an inhibitory RNA (RNAi) that performs a regulatory function, and in various embodiments is selected from the group consisting of a small inhibitory RNA (siRNA), an RNA that forms a triplex with double stranded DNA, and a ribozyme. Alternatively, the RNA is microRNA that performs a regulatory function. The DNA is, in some embodiments, an antisense-DNA.

Uses of SNAs in Immune Regulation

Toll-like receptors (TLRs) are a class of proteins, expressed in sentinel cells, that plays a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that response to specific oligonucleotide are located inside special intracellular compartments, called endosomes. The mechanism of modulation of TLR 4, TLR 8 and TLR 9 receptors is based on DNA-protein interactions.

Synthetic immunostimulatory oligonucleotides that contain CpG motifs that are similar to those found in bacterial DNA stimulate a similar response of the TLR receptors. Therefore immunomodulatory oligonucleotides have various potential therapeutic uses, including treatment of immune deficiency and cancer. Thus, in some embodiments, a SNA of the disclosure comprises an oligonucleotide that is a TLR agonist.

In further embodiments, down regulation of the immune system would involve knocking down the gene responsible for the expression of the Toll-like receptor. This antisense approach involves use of a SNA of the disclosure comprising a specific hairpin-like oligonucleotide to knock down the expression of any toll-like protein. For example, down regulation of a gene responsible for the expression of a Toll-like receptor may be performed using a hairpin-like siRNA-SNA as described herein.

Accordingly, in some embodiments, methods of utilizing SNAs as described herein for modulating toll-like receptors are disclosed. The method either up-regulates or down-regulates the Toll-like-receptor activity through the use of a TLR agonist or a TLR antagonist, respectively. The method comprises contacting a cell having a toll-like receptor with a SNA of the disclosure, thereby modulating the activity and/or the expression of the toll-like receptor. The toll-like receptors modulated include one or more of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and/or toll-like receptor 13.

EXAMPLES

Example 1

Figure 1:
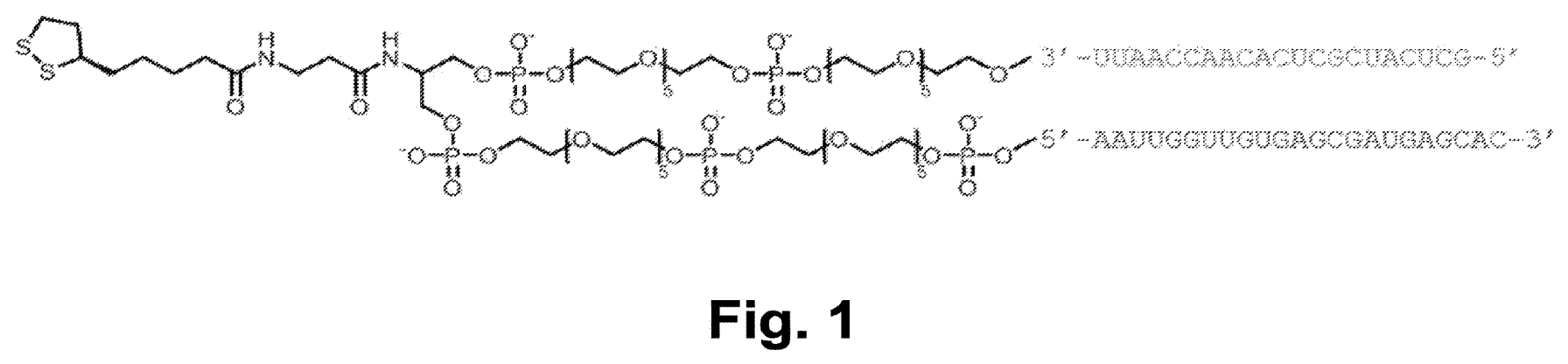

Hairpin-like siRNA oligonucleotides (FIG. 1) were synthesized via the phosphoramidite method from the 3' end to the 5' end. Synthesis started by building the guide strand from the 3' end to the 5' end, followed by spacers, an amidite designed for conjugation to the nanoparticle core, more spacers, and finally the passenger strand from the 3' to the 5' end. Hairpin-like siRNA was isolated by high-performance liquid chromatography (HPLC). The guide and passenger strand hybridized to form duplexed siRNA during synthesis, but hybridization may be enhanced by heating to 95° C. in duplex buffer and slow-cooling to room temperature. Native polyacrylamide gel electrophoresis (PAGE) can be used to determine if the hairpin-like siRNA is hybridized.

Figure 15:
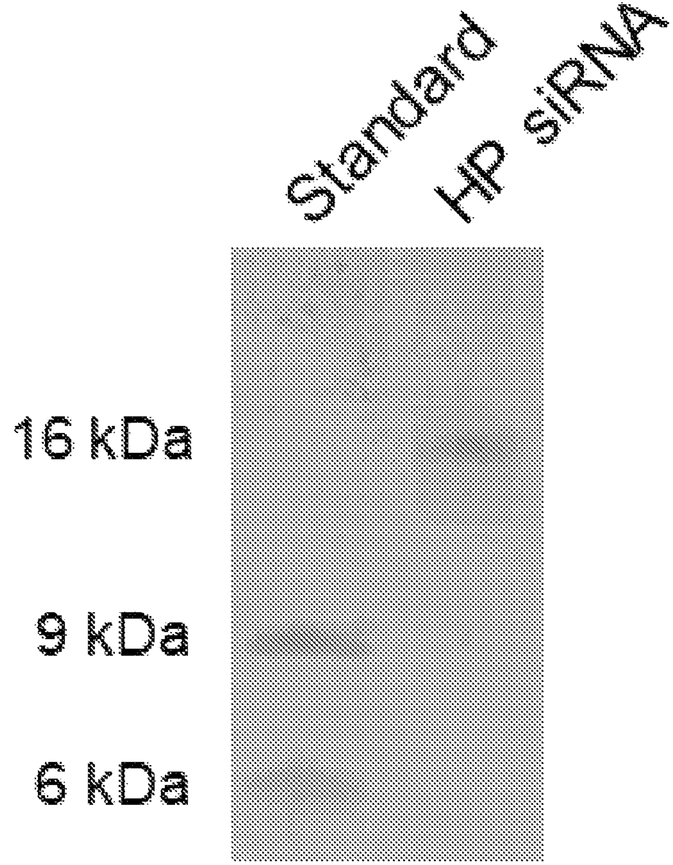
FIG. 15 shows denaturing polyacrylamide gel electrophoresis (PAGE) analysis of hairpin-like siRNA mass. The band location matches the expected molecular weight of 15.9 kDa.
Figure 16:
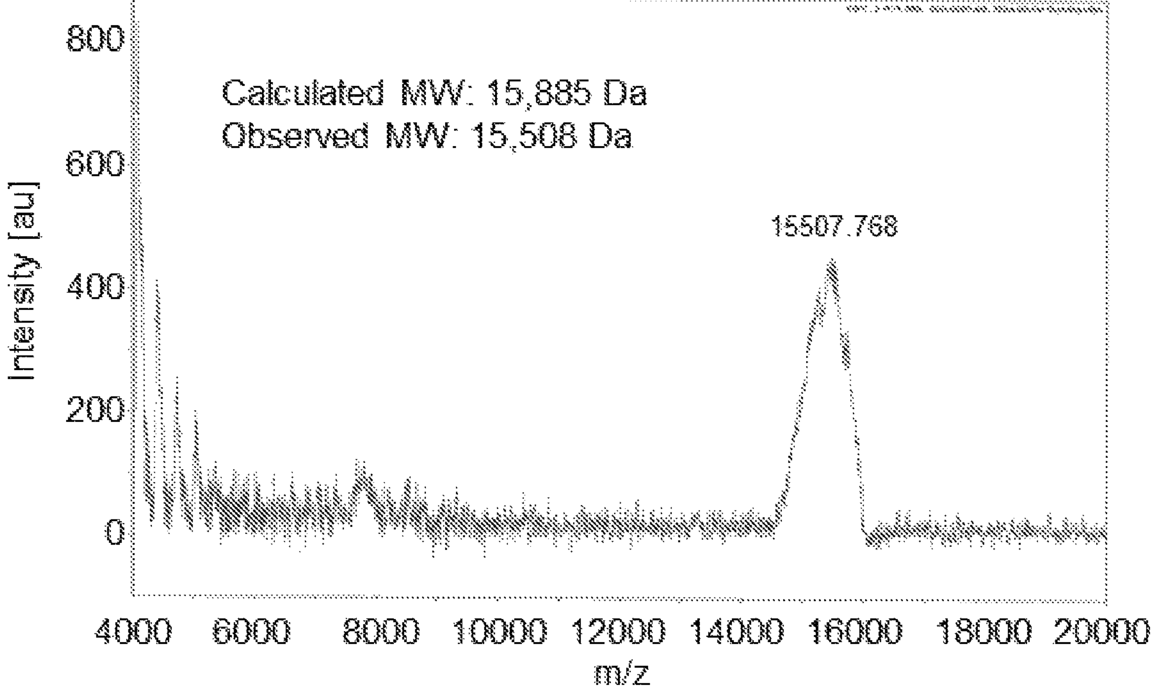
FIG. 16 shows Matrix assisted laser desorption/ionization (MALDI) measurement of hairpin-like siRNA mass. The peak measurement matches the expected molecular weight.

Experiments were performed to analyze the mass of hairpin-like siRNA. Denaturing PAGE: A 6 kDa, 9 kDa standard and the hairpin-like siRNA were ran through a denaturing PAGE gel. A 588-593 methylene blue stain was used to stain the RNA. PAGE gel results are shown in FIG. 15. MALDI: Hairpin-like siRNA was mixed with 2',4',-dihydroxyacetophenone (DHAP) MALDI matrix on a MALDI chip and allowed to dry. MALDI was performed using an Autoflex III Smartbeam MALDI-time of flight (TOF) mass spectrometer. Results of MALDI analysis are shown in FIG. 16, and demonstrated that both methods showed that the hairpin-like siRNA had the expected (calculated) mass.

Figure 17:
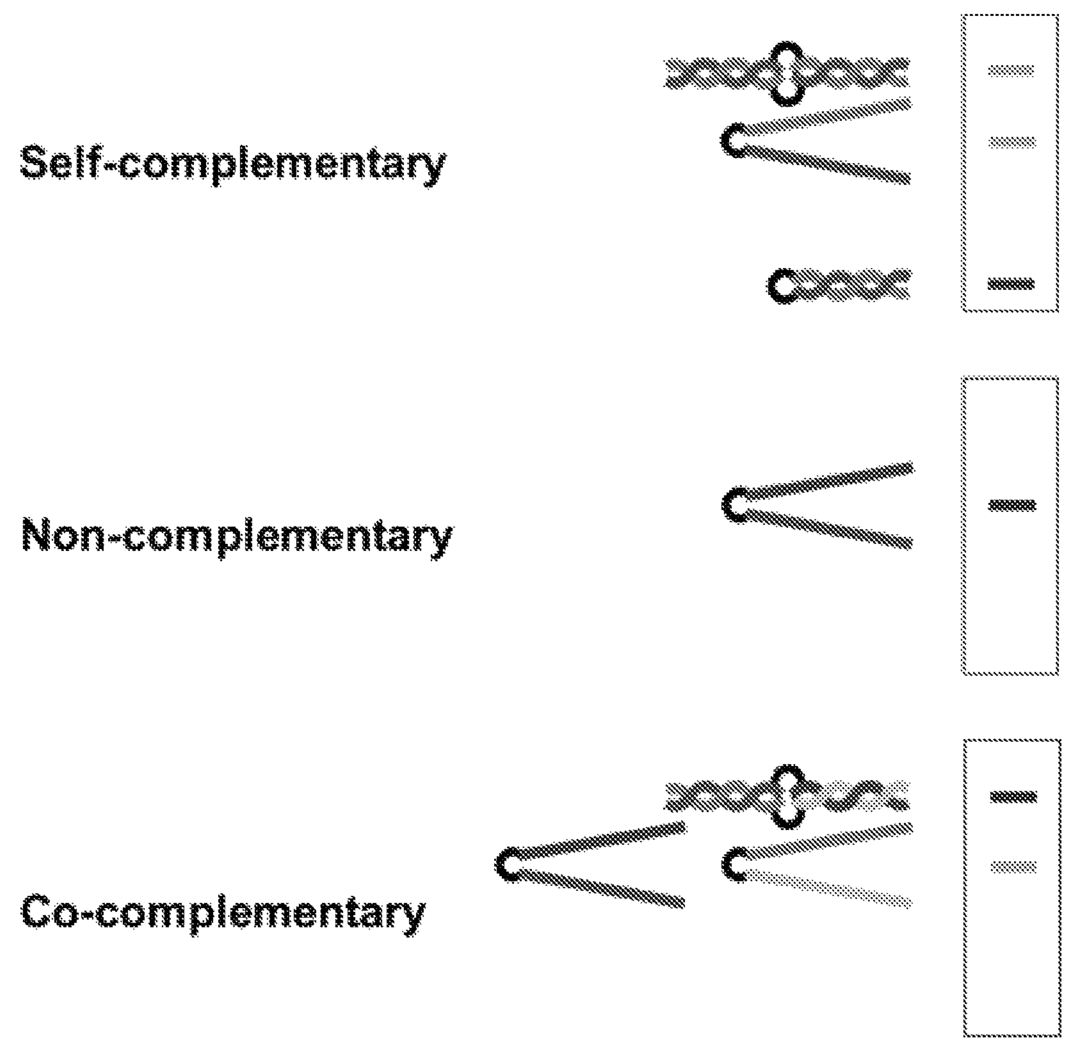
FIG. 17 depicts versions of hairpin-like siRNAs that were tested. Experimental results are shown in FIG. 18.
Figure 18:
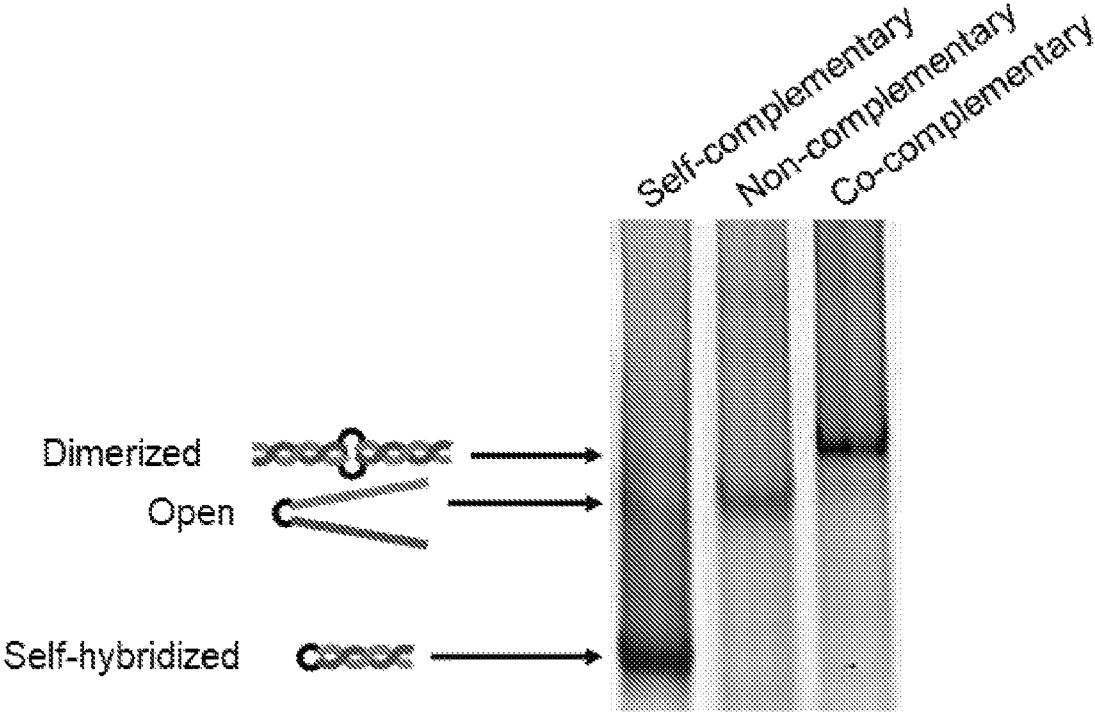
FIG. 18 shows native polyacrylamide gel electrophoresis (PAGE) analysis of hairpin-like siRNA conformation. The non-complementary well shows the location of the open conformation band, and the co-complementary well shows the location of dimer conformation band. For the self-complementary hairpin-like siRNA, the dominant conformation is self-hybridization, indicating that the hairpin-like siRNA is able to efficiency self-hybridize into the hairpin siRNA duplex necessary for gene silencing functionality.

To investigate if hairpin-like siRNAs were able to self-hybridize to form the hairpin siRNA duplex necessary for gene silencing functionality, instead of remain open or dimerize to other hairpin-like siRNA molecules, several versions of hairpin-like siRNAs were synthesized and analyzed using native PAGE. See FIG. 17. The self-complementary hairpin-like siRNA was the standard design, in which both strands are complementary, and can exist in the three previously listed conformations. The non-complementary hairpin-like siRNA had its strands not complementary to each other, preventing hybridization and only existing in the open conformation. The co-complementary hairpin-like siRNAs each contained strands that were not complementary within the molecule, but the entire length of one siRNA was complementary to the entire length of the other siRNA, which allowed them to hybridize to each other to form the dimerized conformation. The non-complementary and co-complementary hairpin-like siRNAs served as controls to identify the dominant conformation of the self-complementary hairpin-like siRNA. FIG. 18 shows the results of the analysis of the various hairpin-like siRNA conformations. Co-complementary siRNA hybridization: The two co-complementary hairpin-like siRNAs were mixed together at an equal molar ratio in 30 mM 4-(2-hydroxyethyl)-1-piperazineethanesulfonic acid (HEPES) (pH 7.3), 100 mM KOAc, 2 mM MgOAc. The solution was heated to 95° C. for 2 minutes, then slow cooled to room temperature. Native PAGE: RNA samples were mixed with a loading dye and ran through a 10% native PAGE gel at 150 V for 45 minutes. SYBR Gold was used to stain the RNA. The gel was imaged using an Amersham Typhoon biomolecular imager. By using the non-complementary hairpin-like siRNA to identify the open conformation band and the co-complementary hairpin-like siRNAs to identify the dimerized conformation band, it was clear that the most intense band for the self-complementary hairpin-like siRNA is neither of these, but rather the self-hybridized conformation. For the self-complementary hairpin-like siRNA, the dominant conformation was self-hybridization, indicating that the hairpin-like siRNA was able to efficiently self-hybridize into the hairpin siRNA duplex necessary for gene silencing functionality.

Hairpin-like siRNA-conjugated SNAs were synthesized via the salt-aging method. Hairpin-like siRNA, an optional surfactant (e.g., SDS or Tween-20 (polyethylene glycol (20) sorbitan monolaurate)), NaCl, and gold nanoparticles were combined and incubated with shaking. Every few hours, NaCl was added to increase the salt concentration, eventually forming the SNAs (FIG. 2). The SNAs were washed with phosphate-buffered saline (PBS) using a centrifugal filter. The SNAs were further washed via high-speed centrifugation followed by removal of the supernatant to remove free RNA. The foregoing wash methods are interchangeable. Usually only one of the methods is used for washing a single batch of SNAs. Hairpin-like siRNA-conjugated SNAs were characterized by measuring hydrodynamic diameter using dynamic light scattering, zeta potential using a phase analysis light scattering, concentration using UV-Vis spectroscopy, and siRNA loading per nanoparticle using an OliGreen fluorescence assay.

Figure 3:
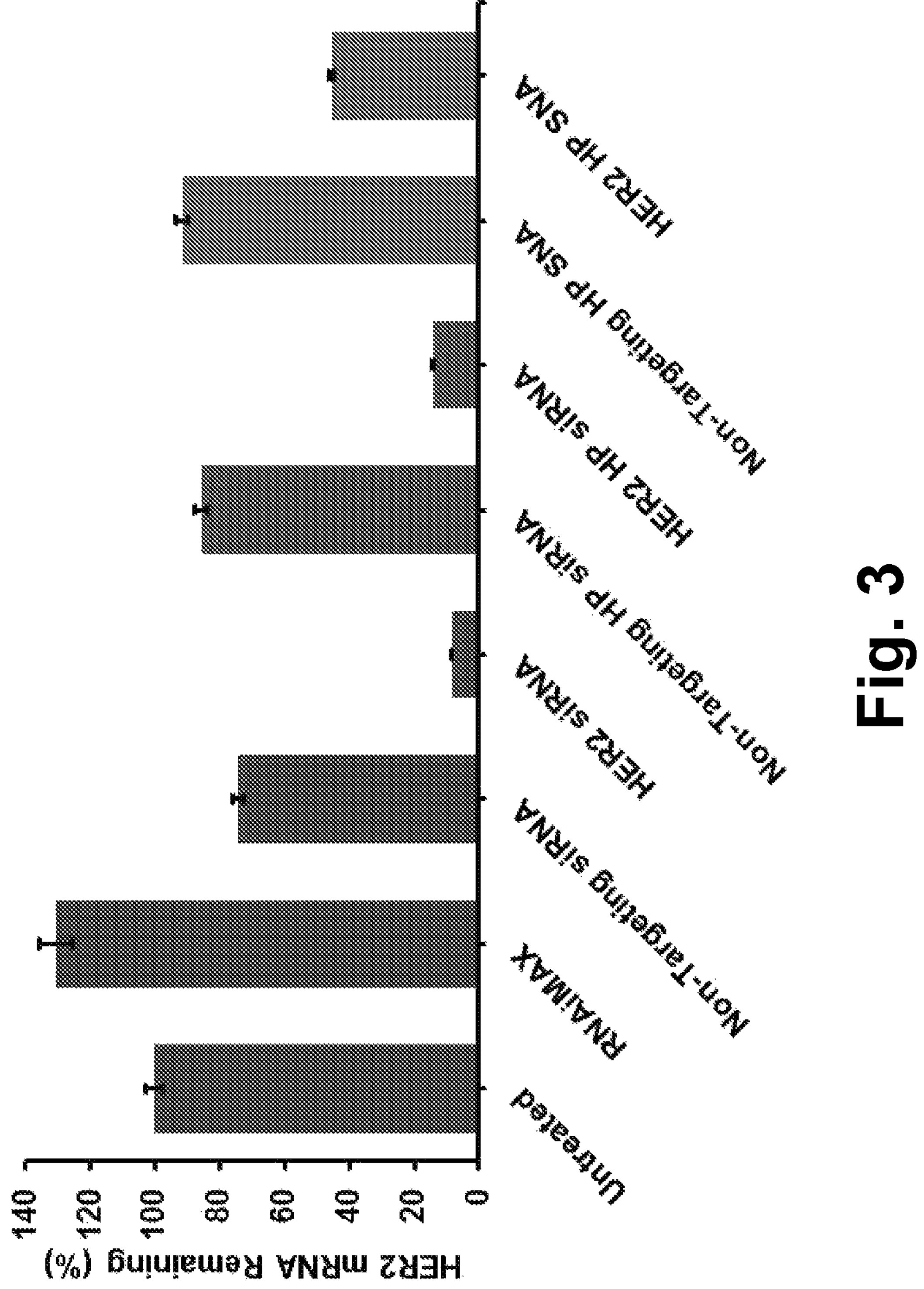
FIG. 3 shows HER2 (human epidermal growth factor receptor 2) knockdown effect of HER2-targeting siRNA, hairpin-like siRNA (HP siRNA), and hairpin-like siRNA-SNA (HP SNA) relative to non-targeting controls in SK-OV-3 cells treated with 100 nM siRNA equivalents for 48 hours as assessed by qPCR. The siRNA and SNAs were transfected with Lipofectamine RNAiMAX.

Gene knockdown in vitro was performed by treating cells with SNAs diluted in reduced serum media. Treatment time can be extended by removing the diluted SNAs after 24 hours and replacing with a serum-containing medium. mRNA is then isolated from the cell, and quantitative polymerase chain reaction (qPCR) was performed to measure the knockdown of target gene mRNA in comparison to a housekeeping gene mRNA. Functionality of hairpin-like siRNA-SNAs was confirmed by knocking down the HER2 gene in vitro (FIG. 3). siRNA, hairpin-like siRNA, and hairpin-like siRNA-SNAs were transfected into SK-OV-3 cells with RNAiMAX and treated for 48 hours.

Sequences that targeted HER2 caused significantly greater knockdown than non-targeting sequences, confirming that hairpin-like siRNA-SNAs possess gene knockdown functionality.

Example 2

Figure 4:
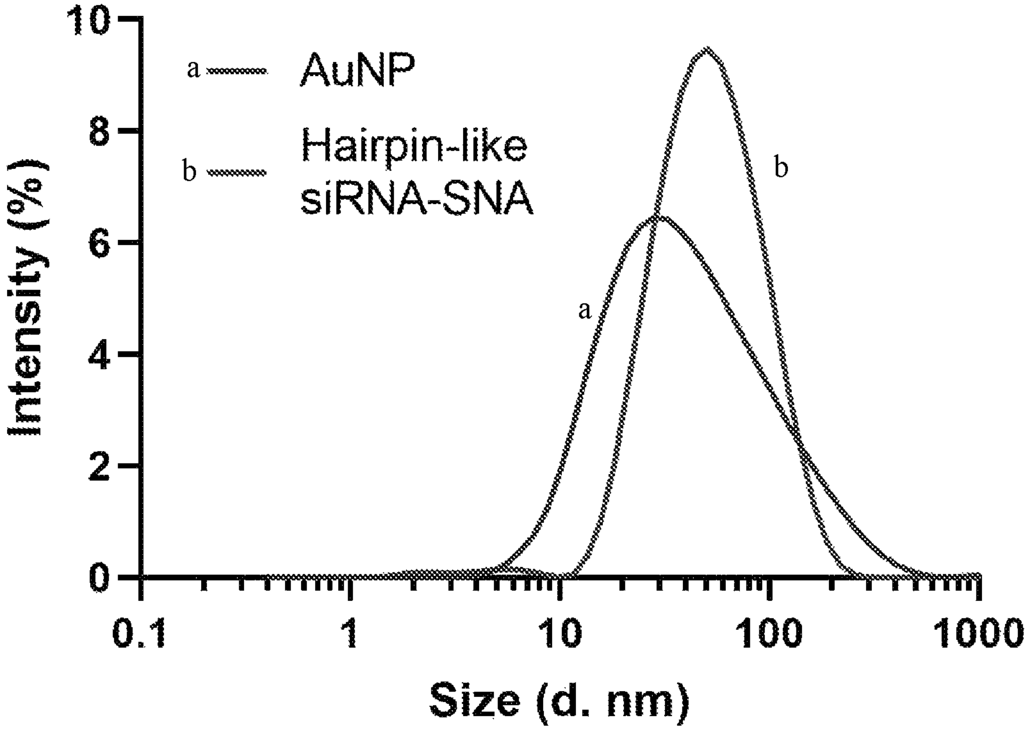
FIG. 4 shows Dynamic Light Scattering (DLS) measurement of the hydrodynamic diameter of the bare gold nanoparticle (AuNP) and hairpin-like siRNA-spherical nucleic acid (SNA). The increase in diameter from AuNP to hairpin-like siRNA-SNA indicated that the hairpin-like siRNAs were successfully attaching to the AuNPs to form a larger SNA.

Experiments were conducted to measure the hydrodamic diameter of bare gold nanoparticle (AuNP) and hairpin-like siRNA-spherical nucleic acids (SNA). For DLS, AuNPs were diluted to 1 nM in water (to maintain colloidal stability, as bare AuNPs are not stable in salt), and SNAs were diluted to 1 nM (by gold) in 1× phosphate-buffered saline (PBS) (to maintain siRNA duplex stability). Samples were placed in a cuvette and DLS was performed using a Malvern Zetasizer. Results are shown in FIG. 4.

Figure 5:
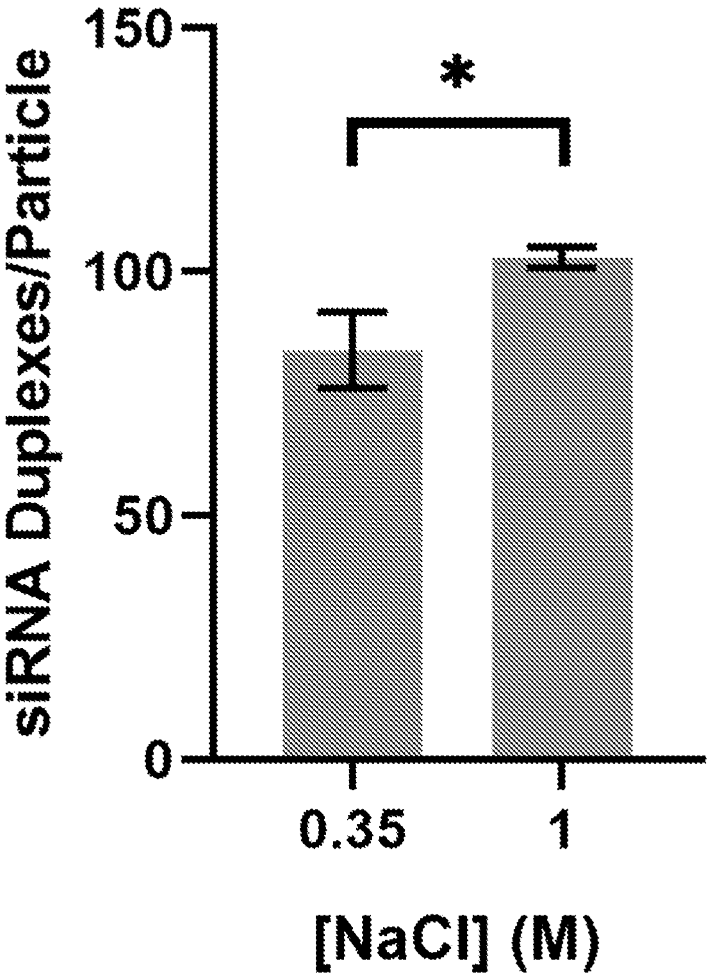
FIG. 5 shows that siRNA duplex loading on hairpin-like siRNA-SNAs was dependent on the final salt concentration during salt-aging. During hairpin-like siRNA-SNA salt-aging synthesis, the salt concentration was gradually increased to screen the repulsive charges of the hairpin-like siRNAs and the AuNP, allowing more hairpin-like siRNA molecules to attach to the AuNP core. Salting to higher concentrations allowed for more hairpin-like siRNA duplexes per SNA, a trend that was consistent with previous observations of other SNAs synthesized via salt-aging. Loading was measured using the Quant-iT OliGreen assay.

Next, experiments were conducted to determine the number of siRNA duplexes on a nanoparticle and the effect of salt concentration on duplex loading. Salt-aging SNA synthesis: 13 nm gold nanoparticles were mixed with Tween-20, 150 mM NaCl, and hairpin-like siRNA and incubated with shaking overnight. The salt concentration was gradually increased by adding salt every 2 hours, and then incubating again overnight. Excess oligonucleotides were removed using a centrifugal filter, and the SNAs were resuspended in 1×PBS and stored at 4° C.

siRNA duplex quantification for hairpin-like siRNA-SNAs: The gold nanoparticle concentration of the siRNA-SNA solution was measured using UV-vis spectroscopy. Then, the SNAs were mixed with potassium cyanide and heated to dissolve the gold. The Quant-iT OliGreen reagent, a fluorescence nucleic acid stain, was added to the dissolved SNA solution in a 96-well plate as well as a standard curve of known hairpin-like siRNA concentrations. A BioTek Cytation 5 imaging reader was used to measure the fluorescence of the SNA solution and standard curve. Through comparing the fluorescence of the SNA solution to the fluorescence of the known hairpin-like siRNA concentrations in the standard curve, the siRNA concentration of the SNA solution was calculated. The siRNA concentration was divided by the gold nanoparticle concentration to determine the number of siRNA duplexes per particle. Results are shown in FIG. 5.

Figure 6:
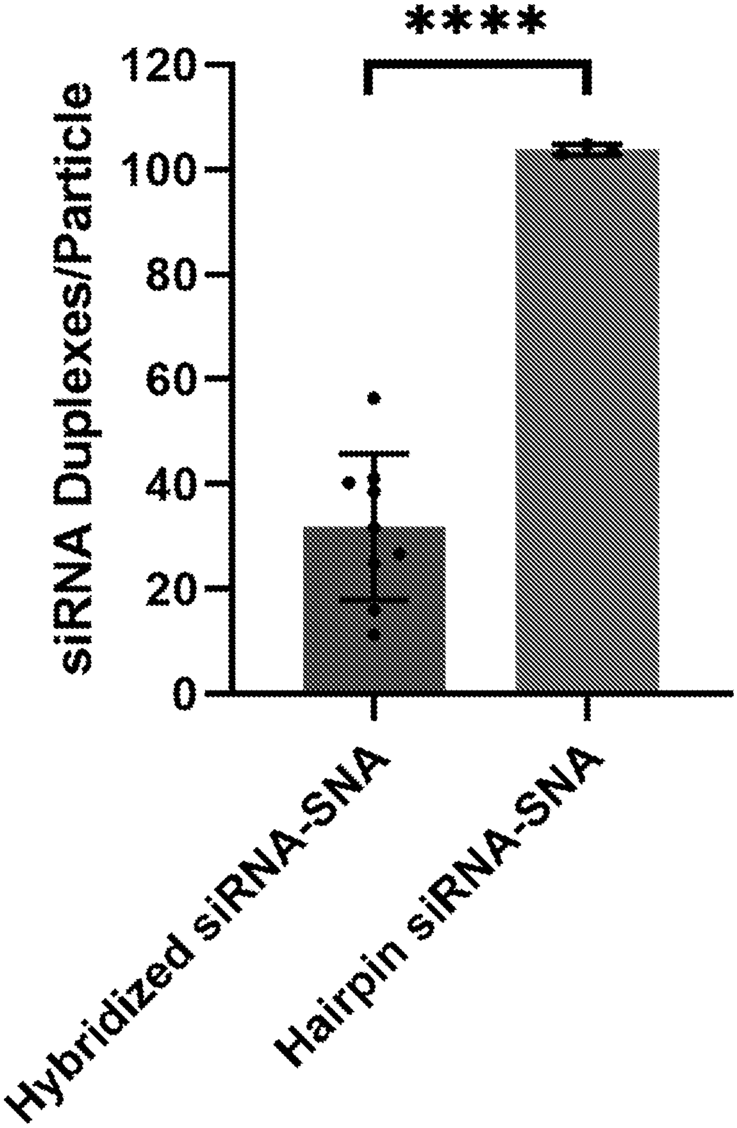
FIG. 6 shows that hairpin-like siRNA-SNAs allowed for the loading of more siRNA duplexes/particle compared to the previously used hybridized siRNA-SNA architecture. Hairpin-like siRNA-SNAs also had lower batch variability of duplex loading compared to hybridized siRNA-SNAs. Both SNAs were synthesized via salt-aging. Loading was measured using the Quant-iT OliGreen assay.

Next, a comparison of the number of siRNA duplexes per particle and the number of hybridized siRNAs was made. Results are shown in FIG. 6. siRNA duplex quantification for hybridized siRNA-SNAs: The gold nanoparticle concentration of the siRNA-SNA solution was measured using UV-vis spectroscopy. Then, the SNAs were mixed with urea and heated to dissociate the siRNA guide strands from the SNA. Tween-20 was added and the SNAs were centrifuged. The supernatant containing the guide strands was transferred to a 96-well plate. The Quant-iT OliGreen reagent was added to the guide strand solution as well as a standard curve of known guide strand concentrations. A BioTek Cytation 5 imaging reader was used to measure the fluorescence of the guide strand solution and standard curve. Through comparing the fluorescence of the SNA solution to the fluorescence of the known guide strand concentrations in the standard curve, the guide strand concentration of the SNA solution was calculated. Since the guide strands were only present on the SNA when attached to the passenger strands to form siRNA duplexes, the guide strand concentration was divided by the gold nanoparticle concentration to determine the number of siRNA duplexes per particle. siRNA duplex quantification for hairpin-like siRNA-SNAs: This method was performed as described above.

Figure 7:
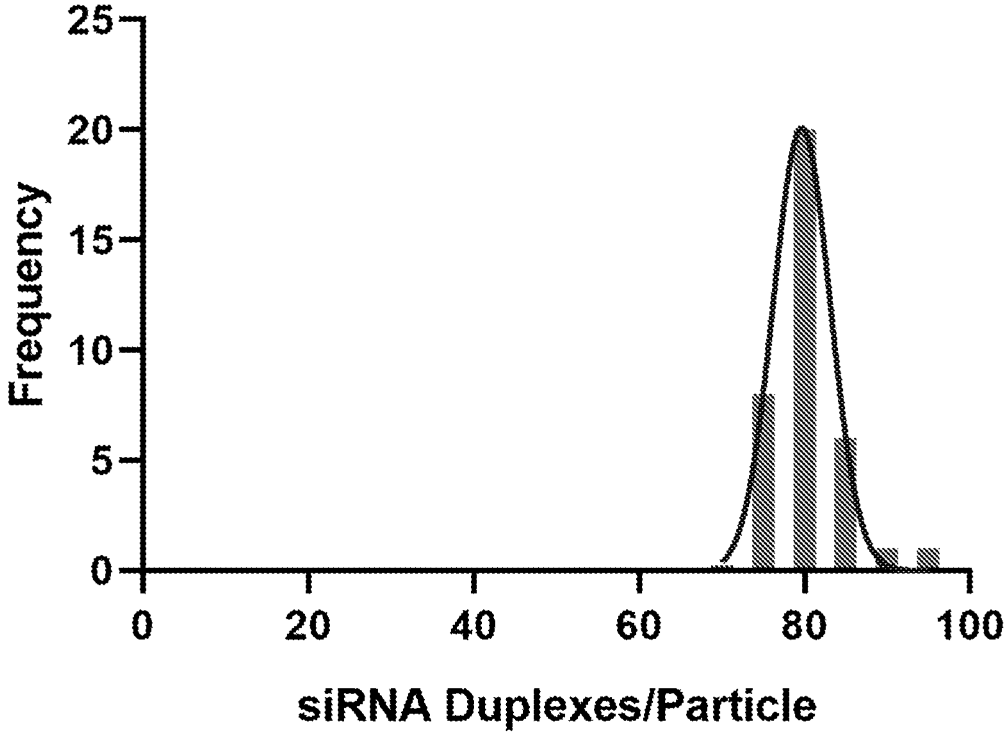
FIG. 7 shows the batch variability of siRNA duplex loading for hairpin-like siRNA-SNAs synthesized via salt-aging.

It appeared from FIG. 6 that the duplex loading of hairpin-like siRNA-SNAs had a lower batch variability than hybridized siRNA-SNAs. To further investigate this, a larger-scale analysis of batch variability was performed and showed that the batch variability of duplex loading was low. This is important because the siRNA duplex is the active ingredient of the SNA drug, and batch variability affects the amount of active ingredient on each nanoparticle. From a therapeutic standpoint, low batch variability makes it easier to control dosing and also understand the amount of core material that is administered with a therapeutic concentration of siRNA. Batch variability was examined by performing a salt-aging SNA synthesis that was similar to the method described above except synthesis was performed at a smaller scale in a 96-well plate and excess oligonucleotides were removed by centrifuging the SNAs and removing the supernatant. siRNA duplex quantification for hairpin-like siRNA-SNAs was performed as described above. Results are shown in FIG. 7, and demonstrate that hairpin-like siRNA-SNAs can be reliably synthesized with a predictable duplex loading every time.

Figure 8:
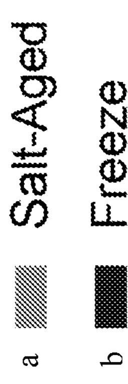
FIG. 8 shows hairpin-like siRNA-SNAs that were synthesized using a salt-aging method or a freezing method. The freezing method is faster and results in similar duplex loading (for HER2 siRNA sequence) or higher duplex loading (for Luc siRNA sequence), depending on siRNA sequence.
Figure 8:
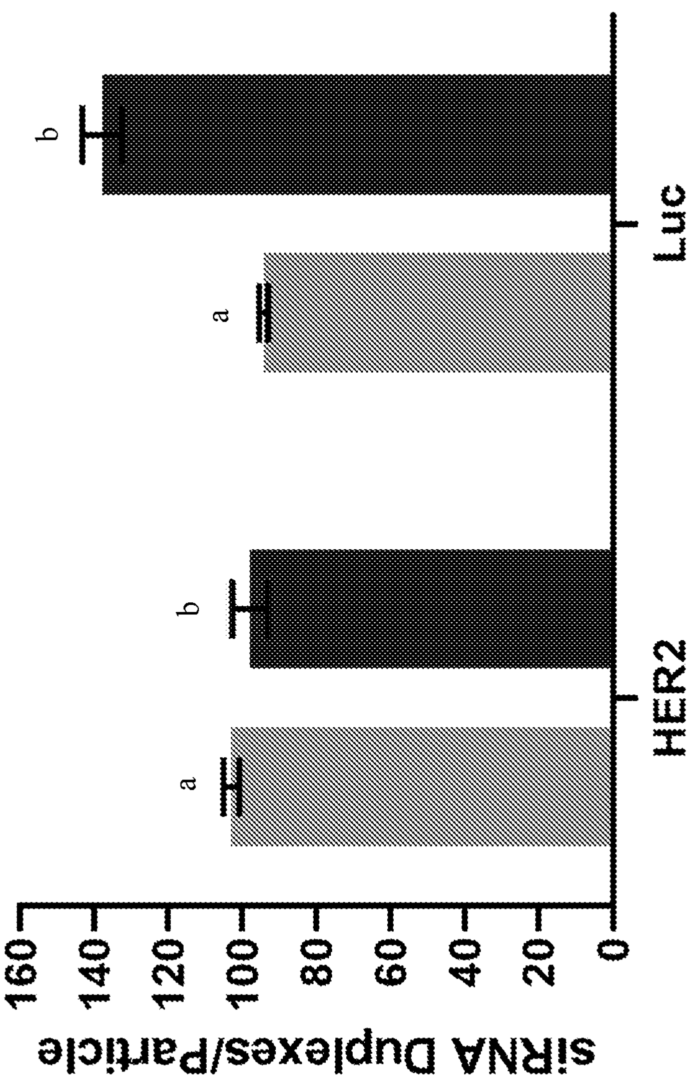

Experiments were performed to compare SNAs synthesized by salt-aging versus freezing method. See FIG. 8. Hairpin-like siRNA-SNAs can be synthesized, for example, using a salt-aging method or a freezing method. The freezing method had previously been demonstrated with single-stranded DNA-based SNAs as a faster alternative to the salt-aging method that does not require salt additions and results in higher DNA loading. It is believed that the freezing method had never before been performed with double-stranded DNA or RNA-based SNAs. Given the high duplex stability of the hairpin-like siRNA, this seemed like an ideal candidate with which to try the freezing method. The salt-aging method involves gradually increased salt concentration to screen the repulsive charges of the hairpin-like siRNAs and the AuNP, allowing hairpin-like siRNA molecules to attach to the AuNP core. The freezing method involves freezing a mixture of hairpin-like siRNAs and AuNPs, during which volume exclusion forces them together to form SNAs, and then thawing at room temperature. The freezing method is faster, and resulted in similar duplex loading (for HER2 siRNA sequence) or higher duplex loading (for Luc siRNA sequence), depending on siRNA sequence. Loading was measured using the Quant-iT OliGreen assay. Freezing SNA synthesis: 13 nm gold nanoparticles were mixed with Tween-20 and hairpin-like siRNA and incubated at −20° C. until the entire solution was frozen. The solution was then thawed at room temperature. Excess oligonucleotides were removed using a centrifugal filter, and the SNAs were resuspended in 1×PBS and stored at 4° C. siRNA duplex quantification for hairpin-like siRNA-SNAs and salt-aging SNA synthesis methods were performed as described above. The results showed that the freezing method can be used to successfully synthesize hairpin-like siRNA-SNAs, and can increase duplex loading compared to the salt-aging method, depending on the siRNA sequence. The freezing synthesis method was developed for hairpin-like siRNA-SNAs as an alternative to the salt-aging method, wherein the freezing method is faster, does not require salt additions, and can result in higher duplex loading.

Figure 9:
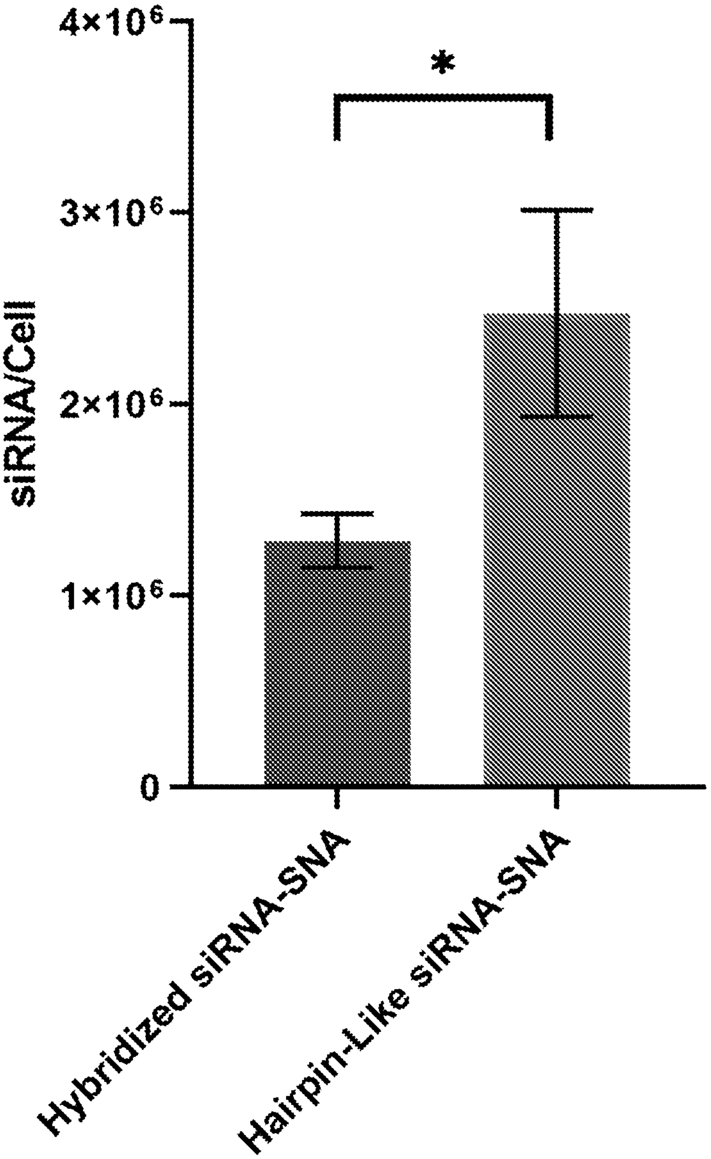
FIG. 9 shows a comparison of the cellular uptake of hybridized and hairpin-like siRNA-SNAs. Hairpin-like siRNA-SNAs deliver more siRNA into cells than hybridized siRNA-SNAs.

To achieve gene knockdown, siRNA has to enter the cell. Higher cellular uptake of SNAs means more siRNA enters the cell and is available to perform gene knockdown. The following experiments were performed to investigate how much siRNA the hybridized siRNA-SNA and the hairpin-like siRNA-SNA are able to transport into cells. The ability of hairpin-like siRNA-SNAs to be taken up by cells was determined and was compared with the cellular uptake of hybridized siRNA-SNAs. See FIG. 9. Cellular uptake treatment: SK-OV-3 cells were treated with 1 nM SNAs in Opti-MEM for 24 hours. Inductively coupled plasma mass spectrometry (ICP-MS): SNAs that remained outside the cells were washed away using 1×PBS. The cells were trypsinized using TrypLE Express. A small portion of cells were stained with Trypan Blue and their concentration was determined using an Invitrogen Countess II automated cell counter. Remaining cells were suspended in 2% HCl, 2% $HNO_3$. The gold concentration within this solution was measured by performing ICP-MS using a Thermo Scientific iCap Q ICP-MS system. The gold concentration was divided by the cell count to determine the number of SNAs per cell, and then converted to siRNA per cell using the measured number of siRNA duplexes per SNA. Methods for siRNA duplex quantification for hairpin-like siRNA-SNAs and siRNA duplex quantification for hybridized siRNA-SNAs were as described above. The results showed that hairpin-like siRNA-SNAs are able to transport more siRNA into the cell than hybridized siRNA-SNAs when treating cells with the same concentration of SNAs.

Figure 10:
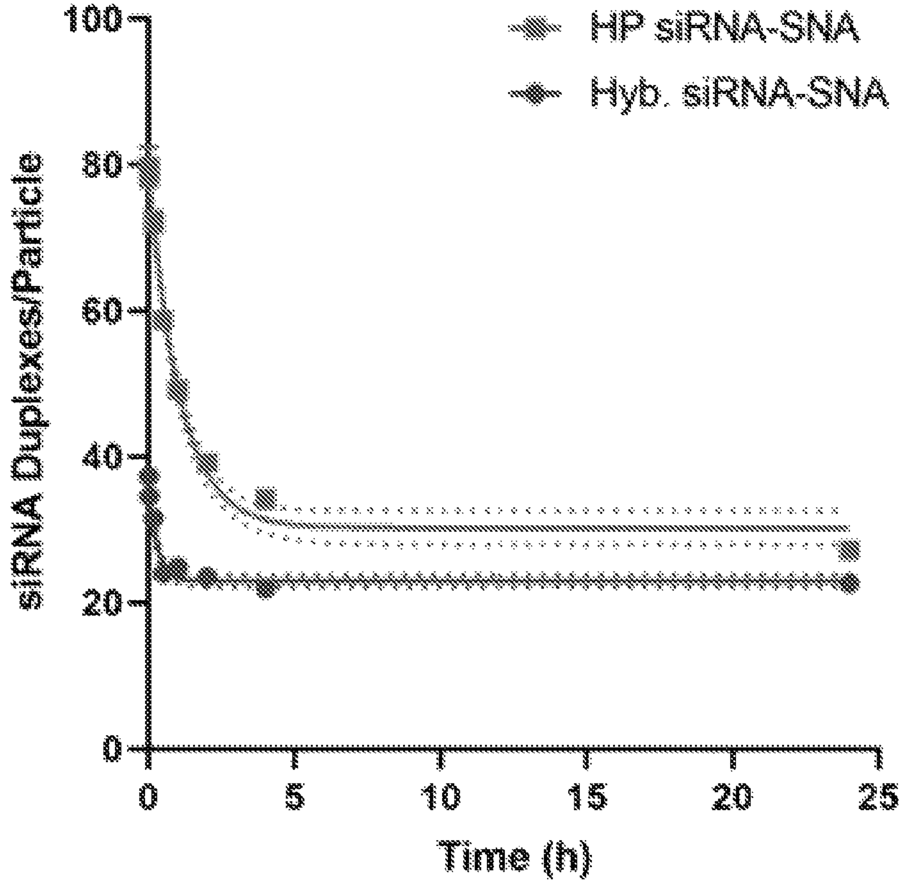
FIG. 10 shows the serum stability of hybridized (hyb.) and hairpin-like (HP) siRNA-SNAs. SNAs were incubated in the presence of serum nucleases and the amount of siRNA duplexes remaining on the SNA was quantified over time. Hairpin-like siRNA-SNAs have a 3.67-fold longer half-life in serum compared to hybridized siRNA-SNAs (12 min vs. 44 min), indicating that the hairpin-like architecture improves siRNA-SNA stability in serum. Loading was measured using the Quant-iT OliGreen assay.

Further experiments were performed to analyze the serum stability of hybridized and hairpin-like siRNA-SNAs. Serum stability assay: SNAs were incubated with 10% fetal bovine serum (FBS) in 1×PBS in 1.5 mL centrifuge tubes at 37° C., allowing the nucleases within the serum to degrade the siRNA. Each tube was incubated for a different amount of time. At the end of each tube's incubation period, sodium dodecyl sulfate (SDS) was added to stop the reaction. The SNAs were then mixed with Tween-20 and centrifuged, and the supernatant containing siRNA fragments released from degraded siRNA was removed. This wash was repeated two more times and the SNA was then resuspended in 1×PBS. The amount of siRNA duplexes remaining on the SNAs was then quantified. Methods for siRNA duplex quantification for hairpin-like siRNA-SNAs and siRNA duplex quantification for hybridized siRNA-SNAs were as described above. Results are depicted in FIG. 10. Serum stability of hybridized (hyb.) and hairpin-like (HP) siRNA-SNAs. SNAs were incubated in 10% fetal bovine serum (FBS), which contains RNases that degrade siRNA, releasing siRNA fragments from the SNA. At several time points, the amount of siRNA duplexes remaining on the SNA was measured. Hairpin-like siRNA-SNAs had a 3.67-fold longer half-life in serum compared to hybridized siRNA-SNAs (12 minutes vs. 44 minutes), indicating that the hairpin-like architecture improved siRNA stability in serum. Loading was measured using the Quant-iT OliGreen assay.

Figure 11:
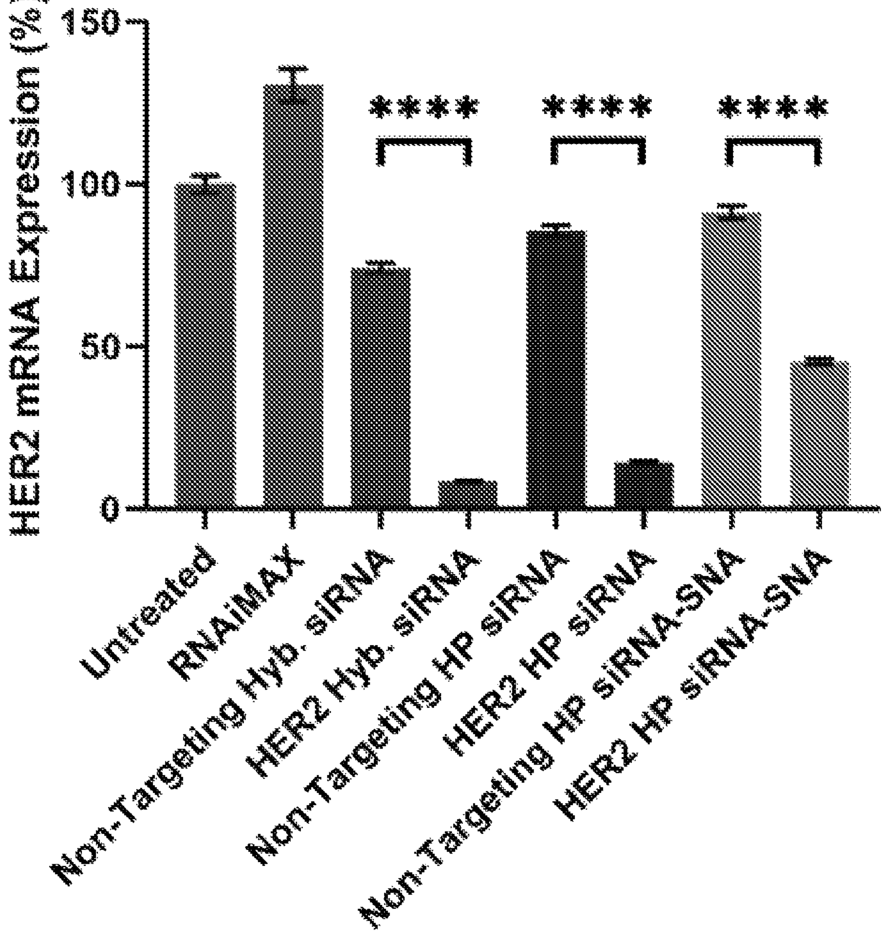
FIG. 11 shows that siRNA with the hairpin-like architecture possesses gene silencing functionality. Different architectures of siRNA that targets the HER2 gene were transfected with RNAiMAX into SK-OV-3 cells to investigate if the hairpin-like architecture allows for gene silencing. The cells were treated with 100 nM siRNA equivalents for 48 hours. The linear forms of hybridized siRNA (hyb. siRNA) and hairpin-like siRNA (HP siRNA), as well as hairpin-like siRNA-SNAs (HP SNA) were able to knock down the expression of the targeted HER2 gene, indicating that the hairpin-like architecture does not prevent gene silencing activity. Gene expression was measured using reverse transcription quantitative polymerase chain reaction (RT-qPCR).

Further experiments were performed to demonstrate that the hairpin-like architecture described herein possesses gene silencing functionality. Gene silencing treatment: 100 nM siRNA concentrations of HER2 targeting and non-targeting linear hybridized siRNA, linear hairpin-like siRNA, and hairpin-like siRNA-SNAs were mixed with Lipofectamine RNAiMAX transfection reagent in Opti-MEM and added to SK-OV-3 cells for 24 hours at 37° C. The treatment solution was then replaced with McCoy's media with 10% FBS, 1% penicillin-streptomycin (Pen-Strep) and incubated at 37° C. for 24 hours. mRNA isolation: mRNA was isolated from cells using a Thermo Fisher Scientific PureLink RNA Mini Kit. Quantitative reverse transcription polymerase chain reaction (RT-qPCR): mRNA isolates were mixed with Quanta Biosciences qScript XLT One-Step RT-qPCR ToughMix and FAM-labeled HER2 and VIC-labeled GAPDH Thermo Fisher Scientific TaqMan probes, then amplified and quantified using a Bio-Rad C1000 Touch Thermal Cycler and Bio-Rad CFX384 Real-Time System. Relative HER2 mRNA expression was calculated using the Pfaffl method to normalize CT values to untreated cell mRNA expression and GAPDH (glyceraldehyde 3-phosphate dehydrogenase; a housekeeping gene) mRNA expression. Results are shown in FIG. 11.

Figure 12:
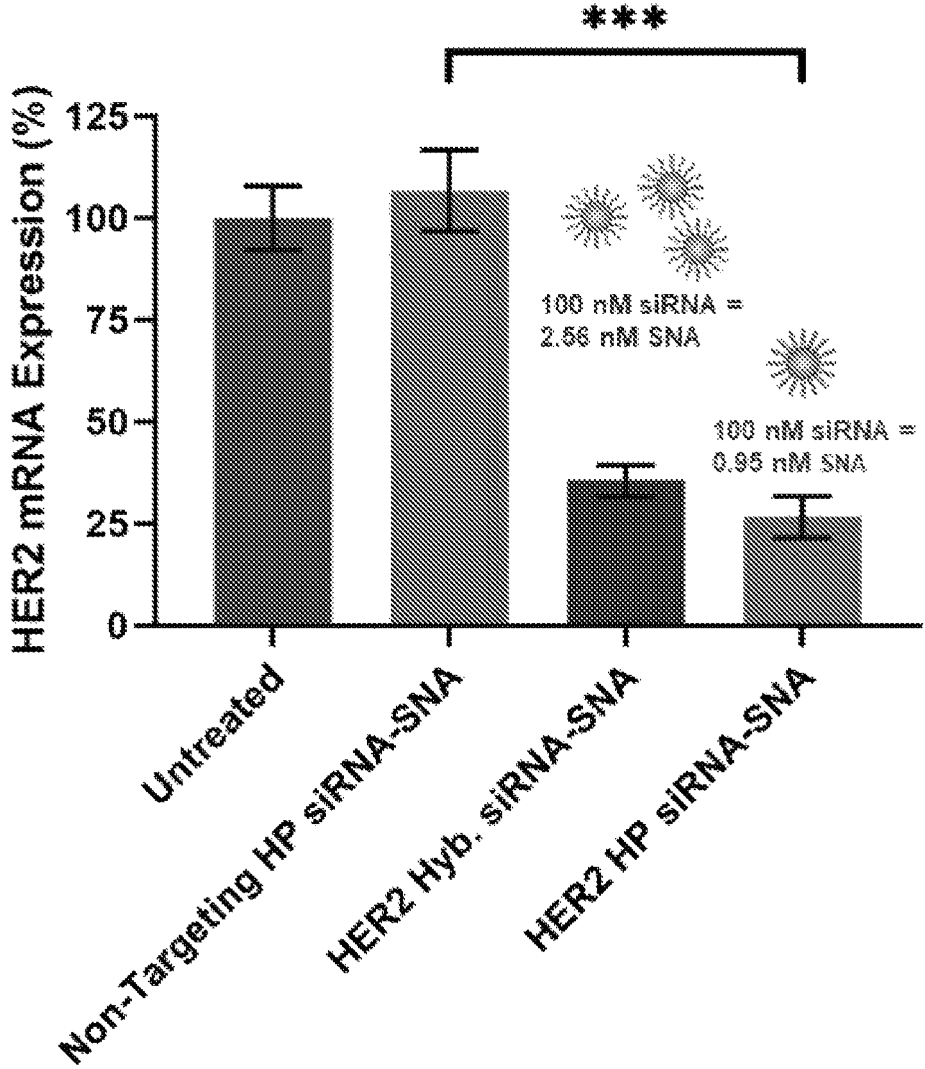
FIG. 12 shows a comparison of gene silencing activity of hybridized and hairpin-like siRNA-SNAs. 100 nM siRNA equivalents of hybridized and hairpin-like siRNA-SNAs were transfected with RNAiMAX into SK-OV-3 cells and the cells were incubated for 48 hours. The figure shows that hybridized and hairpin-like siRNA SNAs achieved similar gene knockdown. Since hairpin-like siRNA-SNAs have more siRNA per SNA than hybridized siRNA-SNAs, it required fewer SNAs to achieve the same siRNA concentration and same knockdown. Gene expression was measured using reverse transcription quantitative polymerase chain reaction (RT-qPCR).

Experiments were also performed to compare the gene silencing activity of hybridized and hairpin-like siRNA-SNAs. Gene silencing treatment: 100 nM siRNA concentrations of non-targeting hairpin-like siRNA-SNAs, HER2 targeting hybridized siRNA-SNAs, and HER2 targeting hairpin-like siRNA-SNAs were mixed with Lipofectamine RNAiMAX transfection reagent in Opti-MEM and added to SK-OV-3 cells for 24 hours at 37° C. The treatment was then replaced with McCoy's media with 10% FBS, 1% Pen-Strep and incubated at 37° C. for 24 hours. Methods of mRNA isolation and quantitative reverse transcription polymerase chain reaction (RT-qPCR) were performed as described above. Results are depicted in FIG. 12, and show that because hairpin-like siRNA-SNAs have more siRNA per SNA than hybridized siRNA-SNAs, fewer SNAs were required to achieve the same siRNA concentration and same knockdown.

Figure 13:
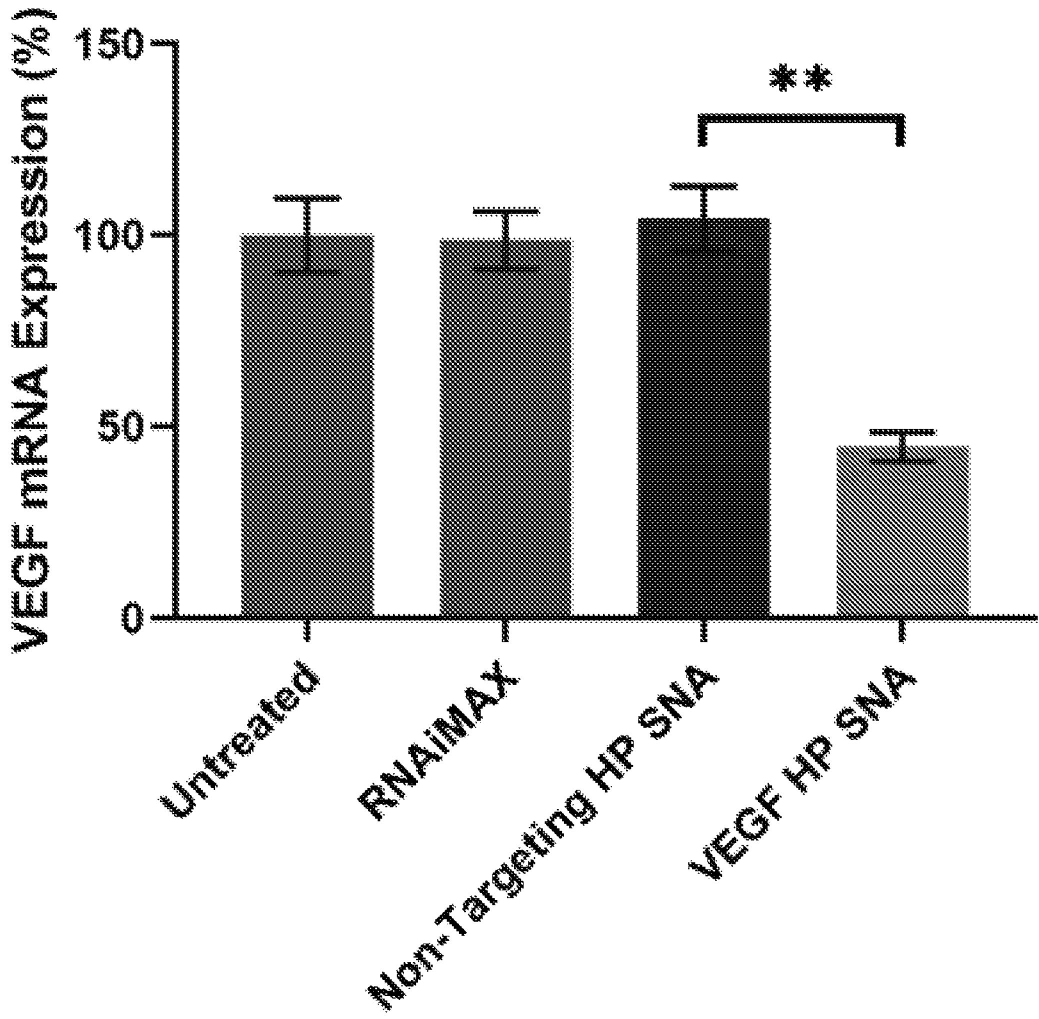
FIG. 13 shows results of experiments in which hairpin-like siRNA-SNAs targeting the VEGF gene were transfected into RAW-Blue cells using a transfection agent (RNAiMAX) and were able to knock down the targeted VEGF gene. Gene expression was measured using reverse transcription quantitative polymerase chain reaction (RT-qPCR).
Figure 14:
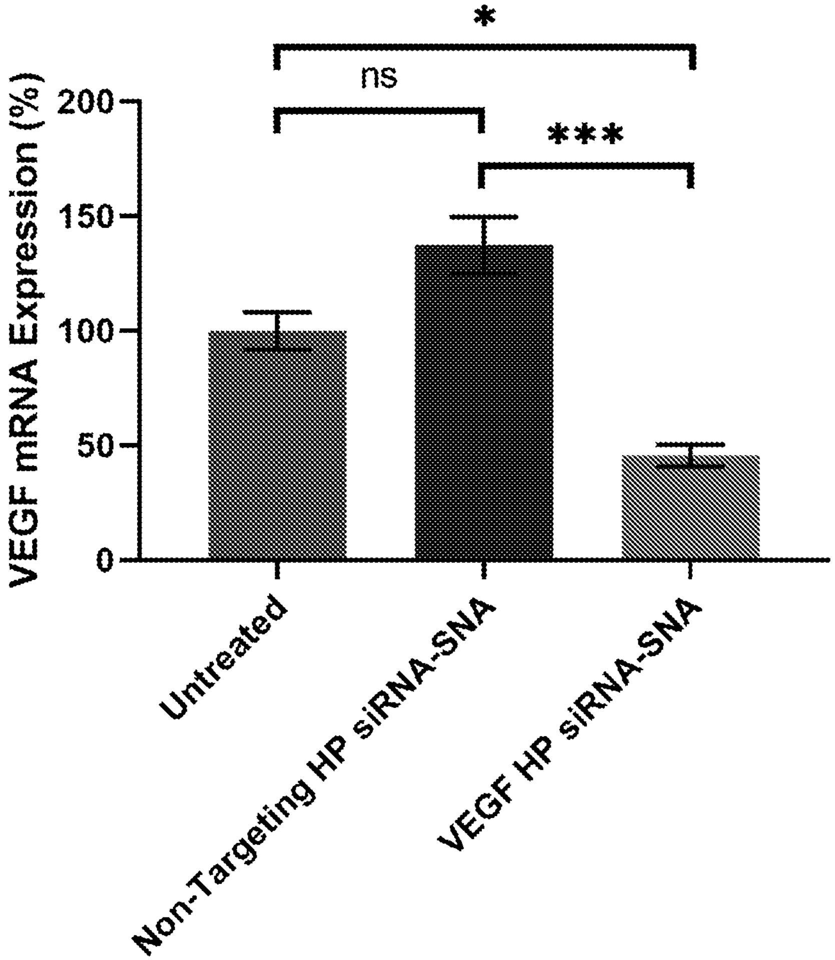
FIG. 14 shows results of experiments in which hairpin-like siRNA-SNAs targeting the VEGF gene were added to RAW-Blue cells and were able to enter the cells and knock down the targeted VEGF gene without the use of a transfection agent. Gene expression was measured using reverse transcription quantitative polymerase chain reaction (RT-qPCR).

Further experiments were performed to show that hairpin-like siRNA-SNAs are able to knock down expression of the VEGF gene without the use of a transfection agent. It was important to demonstrate the full gene silencing functionality of the hairpin-like siRNA-SNA without the need for a transfection reagent. siRNA must enter the cytosol of cells to perform gene knockdown. Linear siRNA cannot enter cells independently, and requires the use of strategies such as co-treating with transfection reagents, such as cationic lipids (including RNAiMAX), to enter cells. Transfection reagents can also be used to improve the cytosolic delivery of SNAs in vitro. However, transfection reagents are cytotoxic, cause off-target effects, and are difficult to characterize. One of the key advantages of siRNA-SNAs is the ability to enter cells and deliver siRNA to the cytosol without the use of a transfection reagent. To compare the level of knockdown achieved with and without use of a transfection agent, experiments were also performed to demonstrate that the level of knockdown achieved with the use of a transfection agent (see FIG. 13) was comparable to the level of knockdown achieved without the use of a transfection agent (see FIG. 14). Compare results shown in FIG. 13 (performed in the presence of a transfection agent) to the results shown in FIG. 14 (performed in the absence of a transfection agent). The treatment conditions used for the experiments leading to the results in FIGS. 13 and 14 were exactly the same, except that RNAiMAX (a transfection agent) was added to the reactions leading to the results shown in FIG. 13. Gene silencing treatment: 50 nM siRNA concentrations of VEGF targeting and non-targeting hairpin-like siRNA-SNAs were prepared in Opti-MEM and added to RAW-Blue cells for 24 h at 37° C. The treatment was then replaced with Dulbecco's Modified Eagle Medium (DMEM) with 10% heat-inactivated FBS, 1% Pen-Strep and incubated at 37° C. for 24 hours. mRNA isolation was performed as described above. Quantitative reverse transcription polymerase chain reaction (RT-qPCR): mRNA isolates were mixed with Quanta Biosciences qScript XLT One-Step RT-qPCR ToughMix and FAM-labeled VEGF and VIC-labeled GAPDH Thermo Fisher Scientific TaqMan probes, then amplified and quantified using a Bio-Rad C1000 Touch Thermal Cycler and Bio-Rad CFX384 Real-Time System. Relative VEGF mRNA expression was calculated using the Pfaffl method to normalize CT values to untreated cell mRNA expression and GAPDH (a housekeeping gene) mRNA expression. Results are shown in FIG. 14.

What is claimed is:

1. A nanoparticle having a substantially spherical geometry comprising an oligonucleotide conjugated thereto, wherein the oligonucleotide comprises a structure as follows:

[nucleic acid sequence 1]—[a first linker]$_x$—[tethering agent]—[a second linker]$_y$—[nucleic acid sequence 2];

nucleic acid sequence 1 and nucleic acid sequence 2 are (i) each RNA; (ii) covalently connected to each other by the first linker, the tethering agent, and/or the second linker; and (iii) are sufficiently complementary to hybridize to each other;

x and y are each independently 0 or 1;

the tethering agent comprises a moiety capable of covalently or non-covalently binding to the nanoparticle surface; and each linker is independently a oligomeric moiety comprising amino acids, nucleic acids, a polymer, or a combination thereof.

2. The nanoparticle of claim 1, wherein nucleic acid sequence 1 has a free 5' end and nucleic acid sequence 2 has a free 3' end.

3. The nanoparticle of claim 1, wherein the polymer comprises ethylene glycol.

4. The nanoparticle of claim 1, wherein x is 1.

5. The nanoparticle of claim 4, wherein the first linker comprises two Spacer-18 moieties.

6. The nanoparticle of claim 1, wherein x is 0.

7. The nanoparticle of claim 1, wherein y is 1.

8. The nanoparticle of claim 7, wherein the second linker comprises two Spacer-18 moieties.

9. The nanoparticle of claim 1, wherein y is 0.

10. The nanoparticle of claim 1, wherein the tethering agent comprises a lipophilic group or a thiol.

11. The nanoparticle of claim 10, wherein the tethering agent comprises dithiol serinol.

12. The nanoparticle of claim 10, wherein the lipophilic group comprises tocopherol or cholesterol.

13. The nanoparticle of claim 1, wherein the nanoparticle comprises a plurality of lipid groups.

14. The nanoparticle of claim 13, wherein at least one lipid group is selected from the group consisting of the phosphatidylcholine, phosphatidylglycerol, and phosphatidylethanolamine family of lipids.

15. The nanoparticle of claim 1, wherein the nanoparticle is metallic.

16. The nanoparticle of claim 1, wherein the nanoparticle is a poly (lactic-co-glycolic acid) (PLGA) nanoparticle.

17. The nanoparticle of claim 1, wherein diameter of the nanoparticle is less than or equal to about 50 nanometers.

18. The nanoparticle of claim 1, wherein the nanoparticle comprises from about 10 to about 200 oligonucleotides.

19. A method of inhibiting expression of a gene, comprising contacting a transcript of the gene with the nanoparticle of claim 1.

20. The method of claim 19 wherein expression of said gene product is inhibited in vivo or in vitro.

* * * * *